(12) United States Patent
Göbel

(10) Patent No.: US 8,900,184 B2
(45) Date of Patent: Dec. 2, 2014

(54) DEVICE FOR STOOL DRAINAGE

(75) Inventor: Fred Göbel, Wilhelmsfeld (DE)

(73) Assignee: Advanced Medical Balloons GmbH (DE)

( * ) Notice: Subject to any disclaimer, the term of this patent is extended or adjusted under 35 U.S.C. 154(b) by 303 days.

(21) Appl. No.: 12/737,011

(22) PCT Filed: May 29, 2009

(86) PCT No.: PCT/EP2009/003855
§ 371 (c)(1),
(2), (4) Date: Mar. 1, 2011

(87) PCT Pub. No.: WO2009/144028
PCT Pub. Date: Dec. 3, 2009

(65) Prior Publication Data
US 2011/0160657 A1    Jun. 30, 2011

(30) Foreign Application Priority Data

May 29, 2008   (DE) .......................... 10 2008 025 779
Jun. 2, 2008    (DE) .......................... 10 2008 026 255
Nov. 3, 2008    (DE) .......................... 10 2008 055 673
Nov. 3, 2008    (DE) .......................... 10 2008 055 674
Feb. 12, 2009   (DE) .......................... 10 2009 008 594
Feb. 12, 2009   (DE) .......................... 10 2009 008 595

(51) Int. Cl.
*A61M 29/00*    (2006.01)
*A61F 5/445*    (2006.01)
*A61M 3/02*     (2006.01)
*A61F 2/00*     (2006.01)

(52) U.S. Cl.
CPC .............. *A61F 5/445* (2013.01); *A61M 3/0295* (2013.01); *A61F 2/0013* (2013.01)
USPC ........................................................ 604/96.01

(58) Field of Classification Search
USPC ................... 604/96.01, 97.01, 99.01, 101.01, 604/101.05, 103.11
See application file for complete search history.

(56) References Cited

U.S. PATENT DOCUMENTS

| 3,889,676 | A | * | 6/1975 | Greene ................... 604/101.05 |
| 4,019,515 | A | * | 4/1977 | Kornblum et al. ....... 604/101.05 |
| 4,117,847 | A | * | 10/1978 | Clayton ..................... 604/97.01 |
| 4,596,554 | A | * | 6/1986 | Dastgeer ...................... 604/540 |
| 4,686,985 | A |   | 8/1987 | Lottick |
| 4,820,270 | A | * | 4/1989 | Hardcastle et al. ........ 604/96.01 |

(Continued)

FOREIGN PATENT DOCUMENTS

| JP | 10-234854 | 9/1998 |
| WO | WO 2006/010556 | 2/2006 |
| WO | WO 2008/103788 | 8/2008 |

*Primary Examiner* — Aarti B Berdichevsky
(74) *Attorney, Agent, or Firm* — Pandiscio & Pandiscio

(57) ABSTRACT

The invention is directed to a device for sealing a natural or artificial opening of the large intestine, or the rectum, of a patient, and for occluding same, and/or for removing stool therefrom, particularly for continuous, and/or intermittent irrigation, preferably into an external, bag-like collection container, comprising an inflatable balloon with an approximately annular structure formed from a flat, everted tube section, wherein the outer layer of the everted tube section is provided with a radially enlarged region for insertion into the rectum, and has a region that is tapered relative thereto, and that remains at least regionally outside the rectum during use, the intrarectal balloon section having no functional or spatial connection to the transanal balloon section.

26 Claims, 22 Drawing Sheets

(56) References Cited

U.S. PATENT DOCUMENTS

| | | | |
|---|---|---|---|
| 5,074,842 A * | 12/1991 | Clayton | 604/514 |
| 5,176,636 A * | 1/1993 | Wild | 604/96.01 |
| 6,409,723 B1 * | 6/2002 | Edwards | 606/41 |
| 7,399,290 B2 * | 7/2008 | Maki et al. | 604/96.01 |
| 7,691,079 B2 * | 4/2010 | Gobel | 604/96.01 |
| 7,914,505 B2 * | 3/2011 | Moeller-Jensen et al. | 604/275 |
| 2002/0173771 A1 * | 11/2002 | Dono | 604/540 |
| 2004/0039348 A1 * | 2/2004 | Kim et al. | 604/264 |
| 2004/0148004 A1 * | 7/2004 | Wallsten | 623/1.11 |
| 2005/0020976 A1 * | 1/2005 | Maki et al. | 604/96.01 |
| 2005/0033226 A1 * | 2/2005 | Kim | 604/101.01 |
| 2005/0113748 A1 * | 5/2005 | Devonec | 604/96.01 |
| 2005/0197531 A1 * | 9/2005 | Cabiri et al. | 600/116 |
| 2007/0213661 A1 * | 9/2007 | Gobel | 604/96.01 |

* cited by examiner

FIG.1a
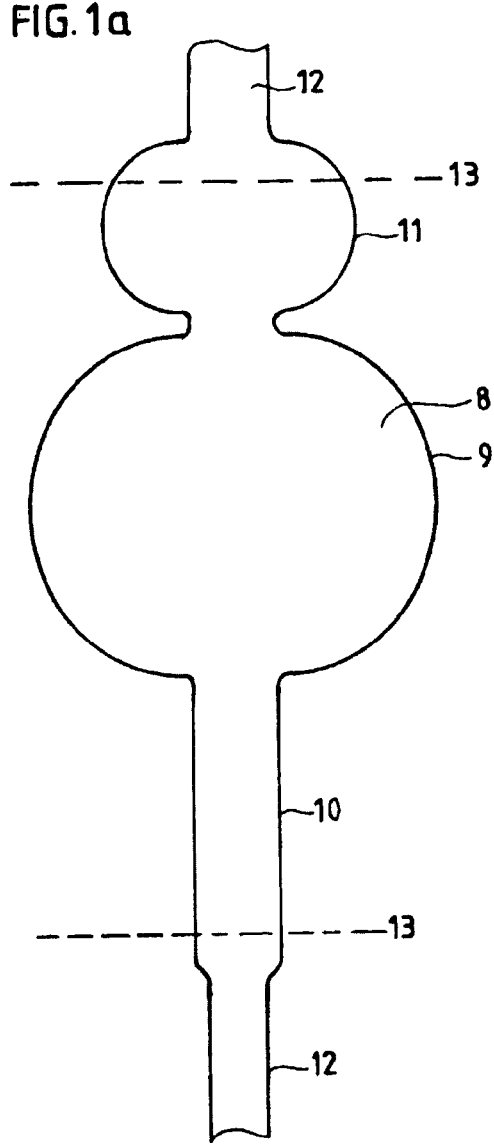
(a)
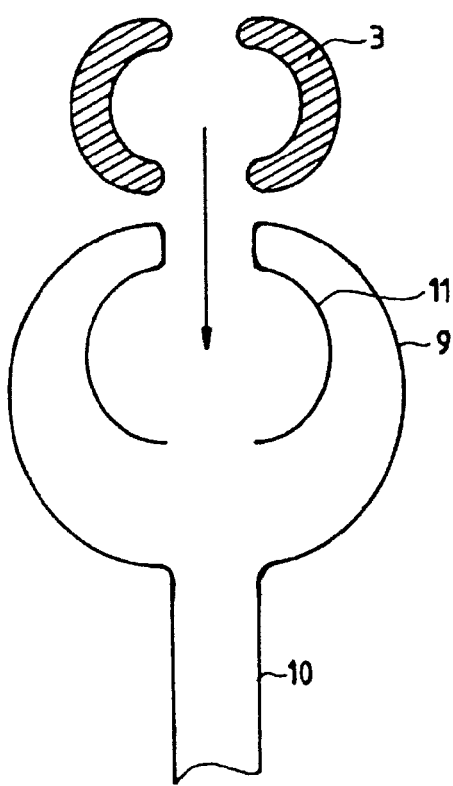
(b)

FIG.1b
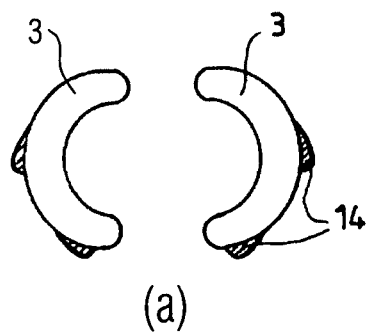
(a)
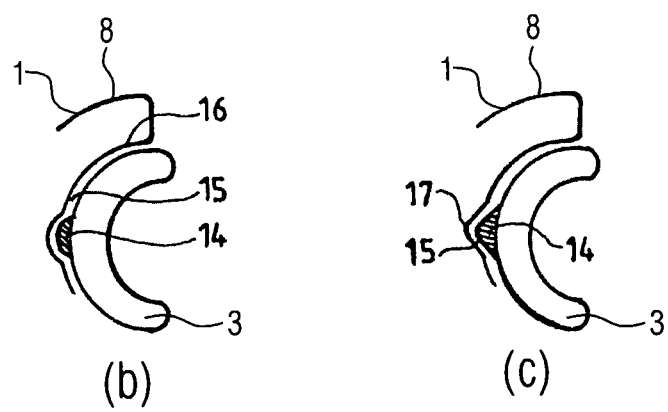
(b)   (c)
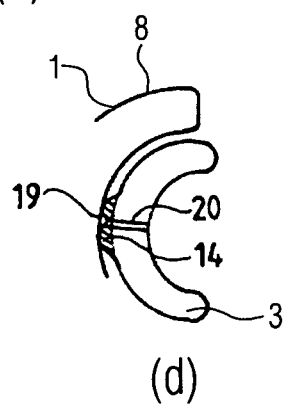
(d)

(a)  (b)

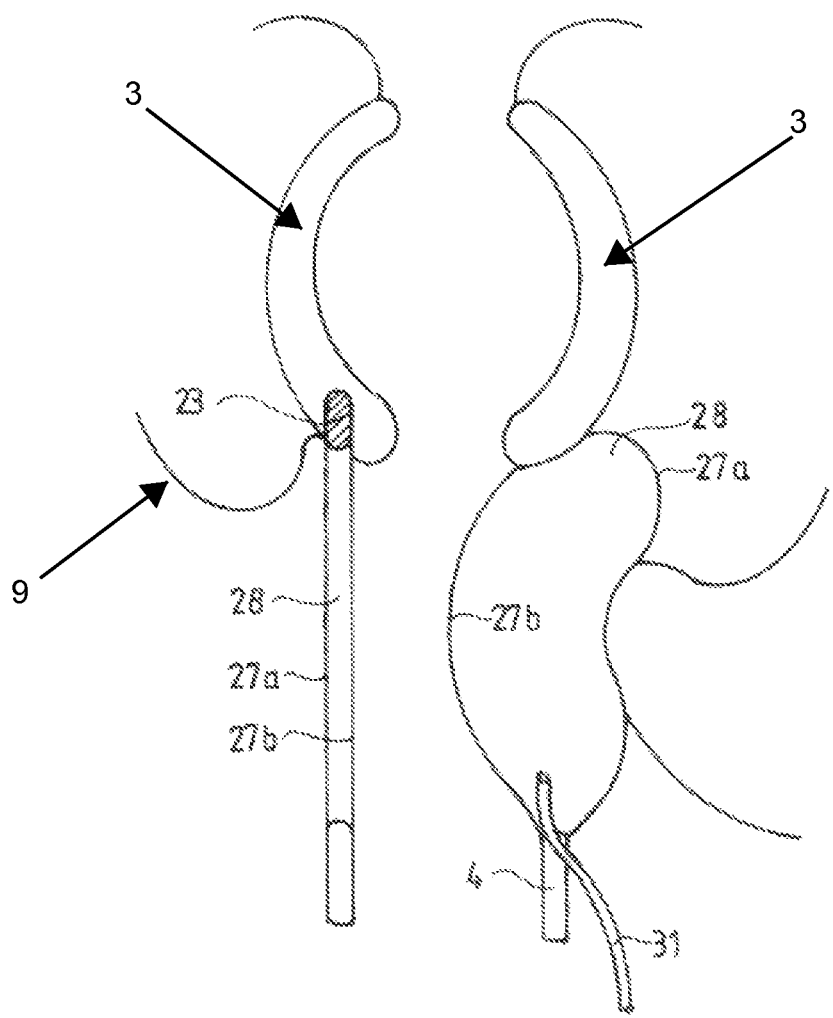

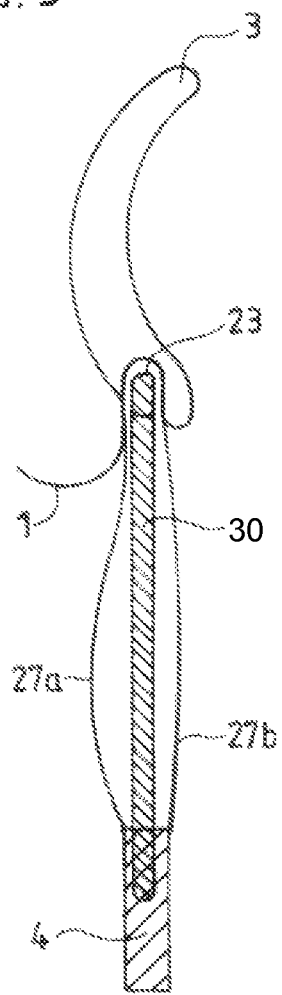

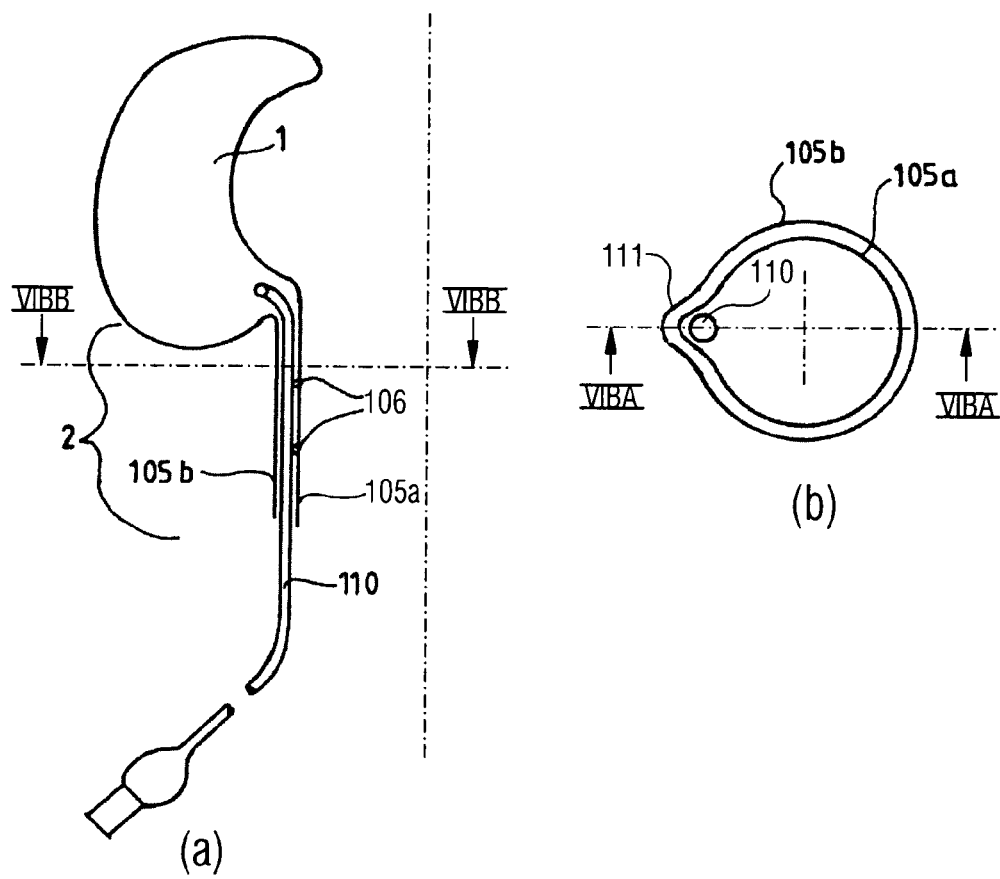

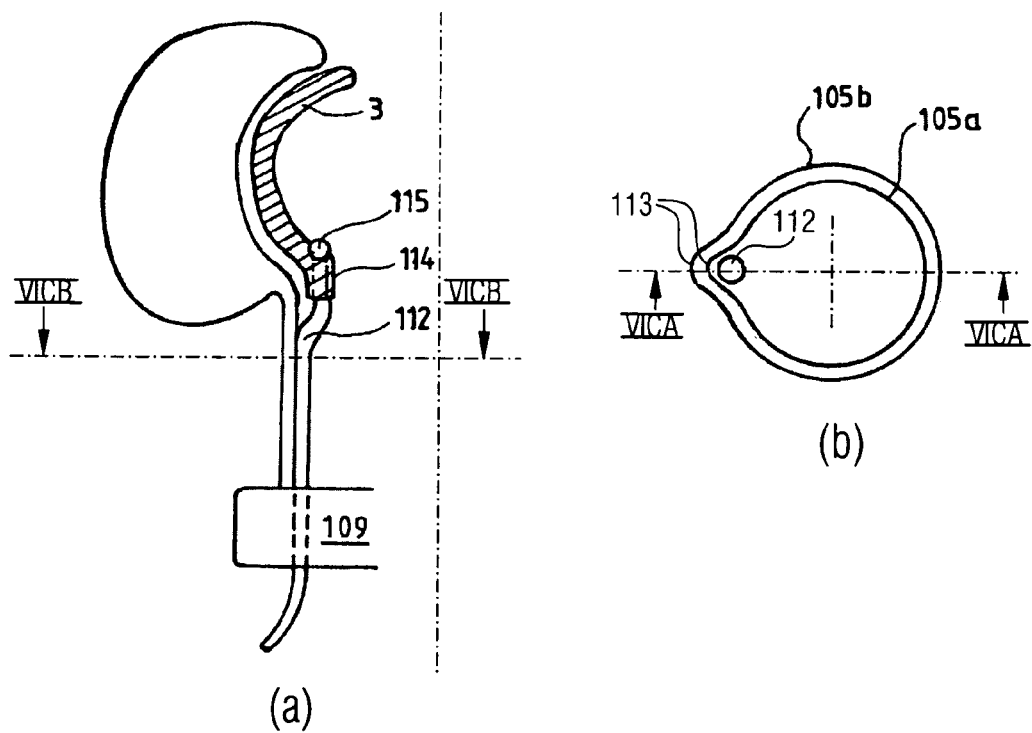

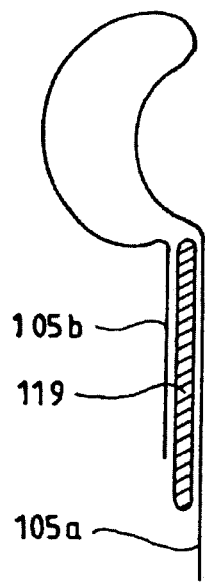
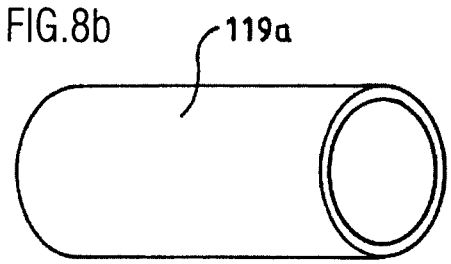
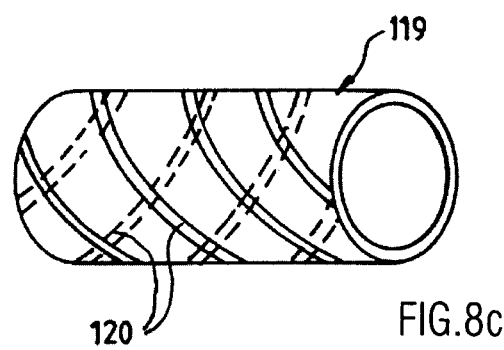

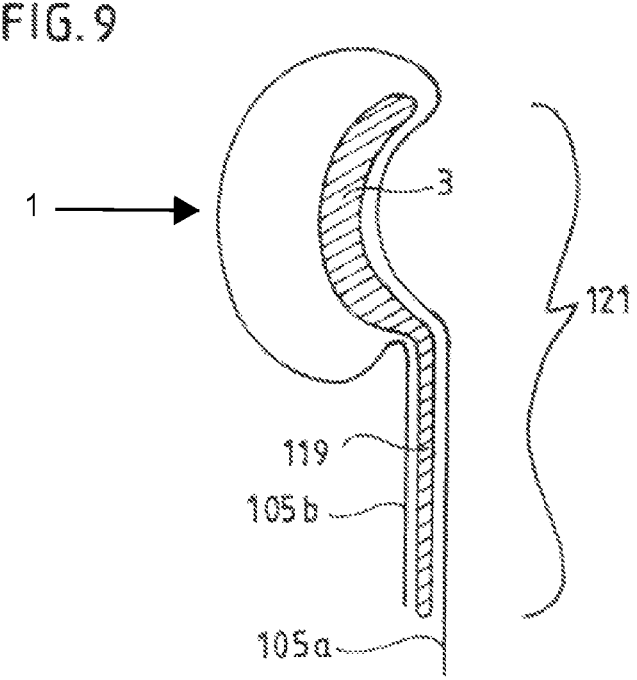

FIG. 11a
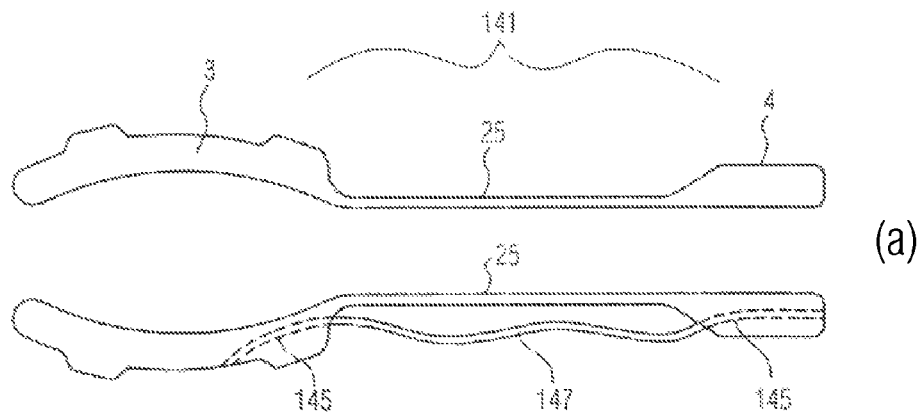
(a)
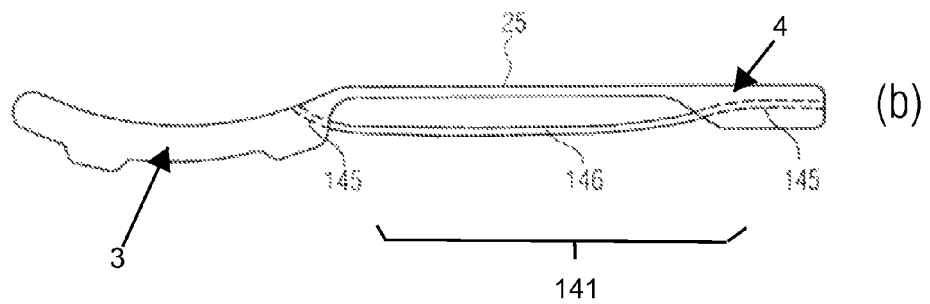
(b)
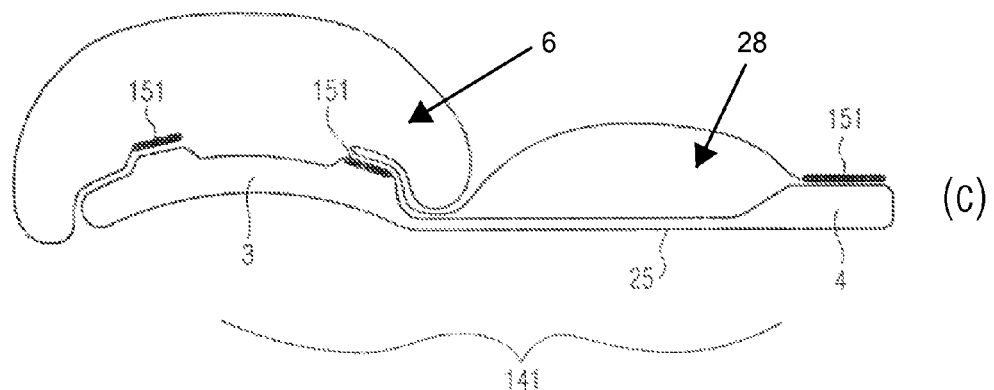
(c)

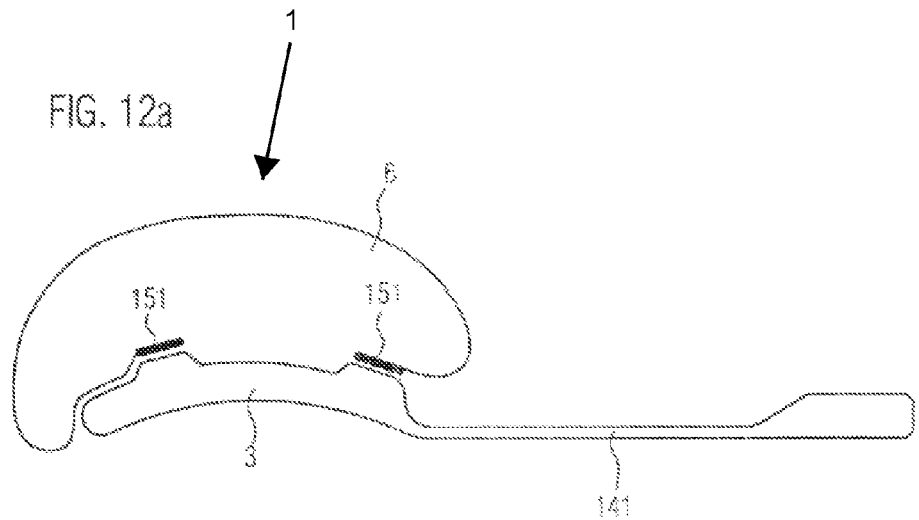
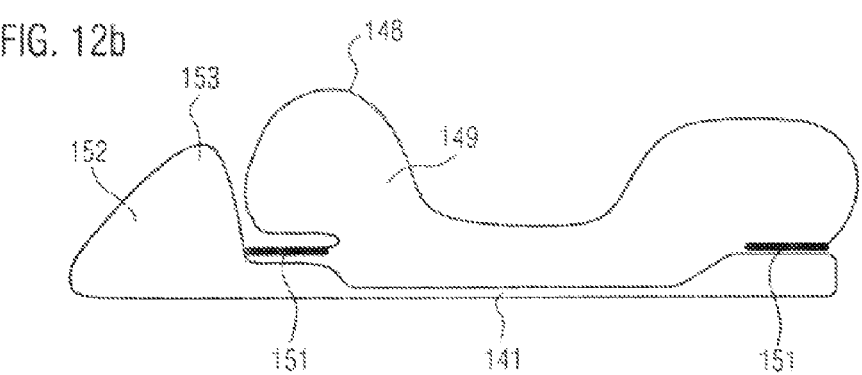

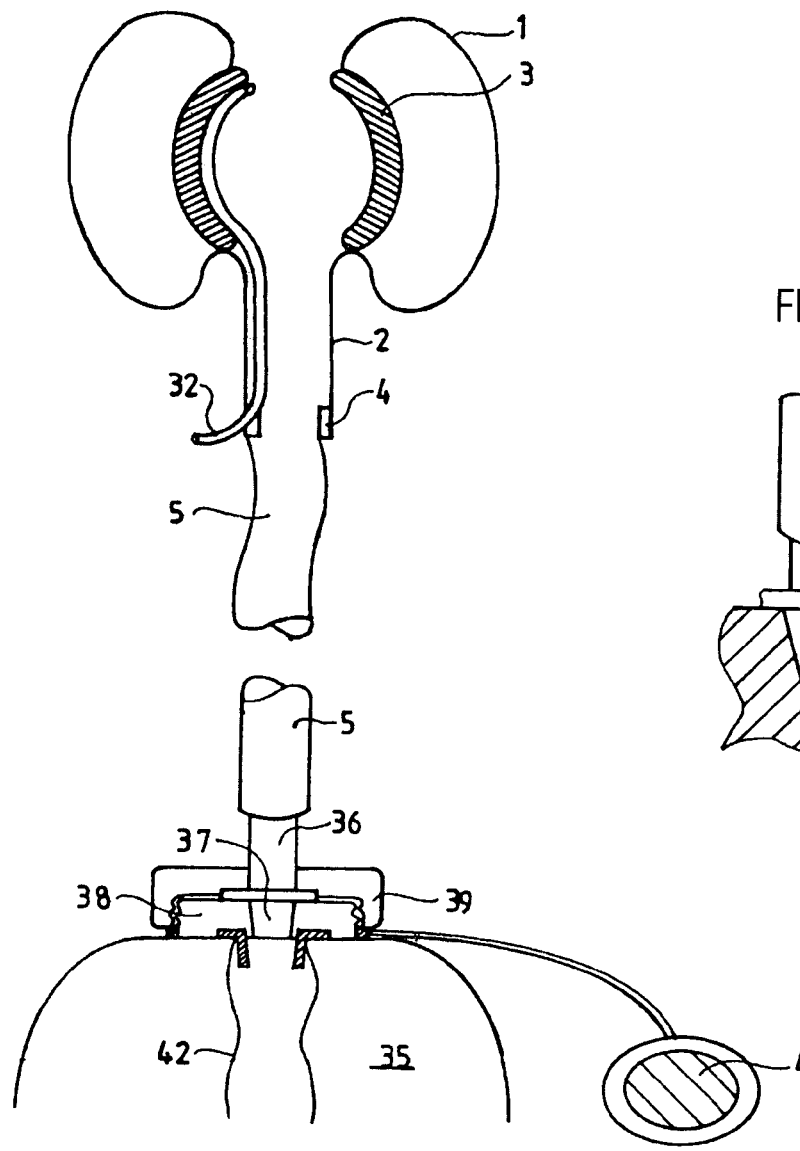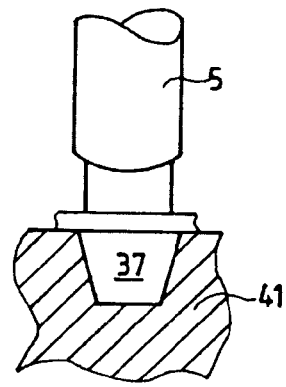

FIG. 14a
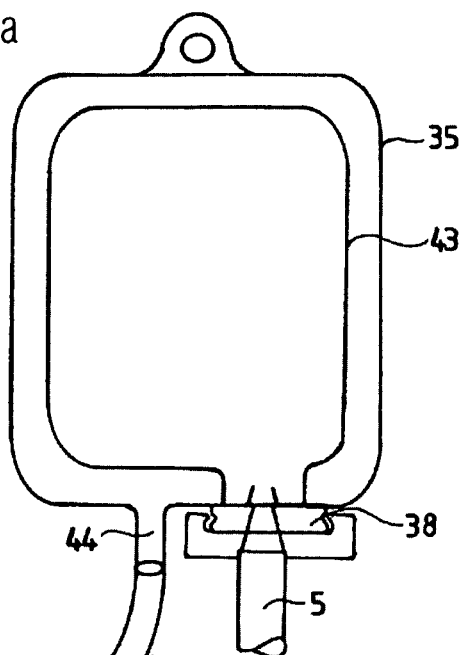
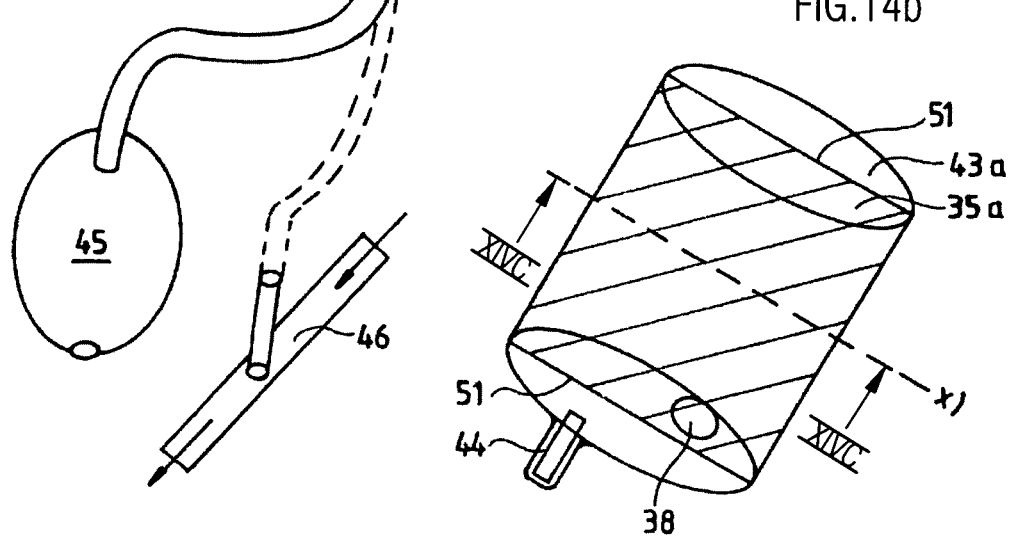
FIG. 14b
x) FIG. 14c
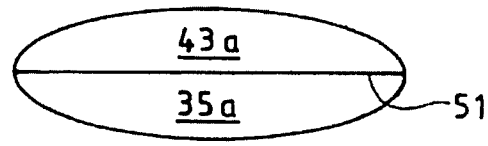

DEVICE FOR STOOL DRAINAGE

CROSS-REFERENCE TO RELATED APPLICATIONS

This application is a national stage filing under 35 USC §371 of International Patent Application No. PCT/EP2009/003855, filed May 29, 2009, which claims foreign priority to German Application No. DE 10 2009 008 595.5, filed Feb. 12, 2009; German Application No. DE 10 2009 008 594.7, filed Feb. 12, 2009; German Application No. DE 10 2008 055 673.4, filed Nov. 3, 2008; German Application No. DE 10 2008 055 674.2, filed Nov. 3, 2008; German Application No. DE 10 2008 026 255.2, filed Jun. 2, 2008; and German Application No. DE 10 2008 025 779.6, filed May 29, 2008.

BACKGROUND OF THE INVENTION

1. Field of the Invention

The invention is directed to a device for sealing, or occluding, an opening of the large intestine (colon), or rectum, of a patient, and, as appropriate, for continuously and/or intermittently draining, or removing, stool therefrom, preferably into an external, bag-like collection container, the device comprising an inflatable balloon with an generally annular structure formed from a flat, everted tube section, wherein the outer layer of the everted tube section is provided with a radially enlarged region (intrarectal balloon portion) for insertion into the rectum and is provided with a region that is tapered relative thereto (transanal balloon portion) and that remains at least regionally outside the rectum during use.

2. Description of the Prior Art

Devices for continuously draining, or intermittently removing, stool from the large intestine (colon), or rectum, of a patient into an external, bag-like collection container, particularly also by means of a rectally administered enema of irrigation fluid, are known.

Drainage, or collection, of stool in the case of immobile, uncooperative patients is preferably carried out with the aid of so-called fecal collectors. These are bag-like structures that are adhesively attached in the anal fold just above the anal opening. Although preanal adhesive attachment is usually sufficiently stable and leaktight for short periods of use, maceration of the exposed skin surfaces is often observed as a result of the continuously moist and chemically aggressive medium in the adhesion area.

An alternative is the use of so-called intestinal tubes, which are inserted through the anal canal into the rectum. Due to the accompanying risk of intrarectal injury, as well as the permanent dilation, and thus the potential for damage to the sphincter muscle, intestinal tubes are normally used for stool drainage only on a temporary basis.

Systems for largely atraumatic stool drainage that can be used over a long term (indwelling fecal drainage), of the kind recently introduced by Zassi Medical Evolutions Inc., Florida, USA, and ConvaTec, New Jersey, USA, are structurally similar in design to balloon catheters for the continuous drainage of urine. Urine is drained from the bladder via a balloon-equipped catheter element, and flows through a connected drainage tube into a collection bag. The balloon element in this case is used primarily to anchor the catheter in the bladder. It also performs a sealing function to some extent, preventing urine from flowing down through the urethra past the shaft of the catheter. Analogously, the known stool drainage systems include a balloon-equipped head portion that anchors the device, collects the stool, and conducts it away, and, connected to this, a tube element that debouches into a collection container.

Modern stool drainage systems, such as the aforesaid, also serve, in addition to the drainage function per se, the purpose of actively managing fecal excretion of the patient within the context of stool management (fecal/bowel management) by therapists.

The concept of stool management includes the option of relatively high-volume or large-volume colorectal irrigation via the anus. Large-volume enemas into the colon have been used for active excretion management in patients with surgically created colostomies. The irrigation fluid injected into the colon mobilizes the contents of the bowel and stimulates intestinal peristalsis, thus causing the colon to largely empty in a manner that is initiated, or triggered, by the user.

Similarly, the contents of the bowel in immobile, uncooperative, bedridden patients can be mobilized and drained by large-volume transanal enema. Defecation is thereby monitored and managed by a therapist. A stool-free, virtually continent interval of one to two days can be achieved in this way.

Colorectal enemas (so-called colorectal irrigation) have been used in clinical practice heretofore primarily to mobilize the stool in the presence of constipation or bowel voiding dysfunction.

The principle of colorectal irrigation has been used successfully in mobile, independent, incontinent patients who, for a wide variety of reasons, have lost ability to evacuate the bowels (defecate) under deliberate control. In these patients, the volume of fluid irrigated into the rectum or colon via the anus has the effect of stimulating intestinal peristalsis, with the objective of emptying the large intestine as completely as possible. The result, for the patient, is a stool-free interval during which there is no possibility of uncontrolled passage of stool through the anus, despite manifest insufficiency of the anal sphincter. Crucial to adequate irrigation is that the injected volume must both mobilize stool in the colon and trigger peristalsis or the defecation reflex. The instillation of the enema solution is usually followed by an interval of several minutes during which the large intestine remains quiet, until peristaltic contractions finally set in and the colon or rectum begins to expel the contents of the bowel. To ensure that the necessary enema volume is retained in the bowel until reflexive expulsion begins, transanally introduced irrigation apparatuses are often equipped with a sealing element. This is usually in the form of a tightly filled balloon that is placed in the terminal rectum; the balloon is mounted on a tube-like inserting element and is designed to keep irrigation fluid from exiting the anus during the waiting period before colonic peristalsis begins.

DESCRIPTION OF THE PRIOR ART

Currently available stool drainage and irrigation systems are problematic in a number of ways:

When the drainage system is left in place for relatively long dwell times of up to several weeks, there is some risk of pressure-induced injury in the region of the terminal rectum (ulcers) and lesions in the region of the anus (fissures). Pressure ulcers are usually the result of tightly filled balloon bodies that anchor the particular device in the rectum, and that remain in continuous contact with the rectal structures and restrict blood flow. The known systems comprise balloons that are only partially preshaped in the unfilled state, and are inflated to their working size by being subjected to about 100 mbar of pressure, so as to ensure their anchoring function. Anal fissures, on the other hand, result in most cases from the constant friction caused in the anus by the more or less rigid transanal drainage portion of the device, which tends to collapse and lie in folds.

Moreover, the known systems do not offer truly adequate sealing performance, especially in the presence of thin stool, or a relatively high-volume flow of irrigation fluid into the colon, thus leading to ongoing fecal incontinence and necessitating meticulous cleaning of the anal folds.

Prior systems tend to slip out of the patient's rectum if pull is exerted on the catheter. This so-called "drop-out" is due in part to the expansion and deformation properties of the materials currently in use, silicone being chief among them. The high compliance of silicone does not allow the balloon to possess adequate dimensional stability, and, when an axial pull is exerted on the drainage system, leads to increasing teardrop-shaped deformation and taper of the balloon anchor, until the latter is so deformed that it prolapses out through the introducing opening that was supposed to be sealed.

Furthermore, conventional elastically expanding anchor balloons do not have a large enough balloon diameter to cover the rectal floor as they lie on it, and thus to achieve the best possible anchoring effect against the anal opening or against axial pull.

To permit long-term catheterization of the particularly sensitive transanal segment with as little trauma as possible, in conventional systems the corresponding segment of the drainage system must be made extremely thin-walled in order for its consistency to be as soft and tissue-friendly as possible. Such a thin-walled implementation of the transanal segment is usually accompanied by a tendency toward torsion or twisting along the longitudinal axis of the transanal segment, thus critically impairing or preventing fecal evacuation.

Moreover, silicones are not odor-tight, and after being in place for a few days usually release a foul fecal odor into the patient's environment. Silicone surfaces are also frequently uneven, and thus, due to a crater-like surface, lead to contamination that is largely resistant to cleaning.

Heretofore available systems made of silicone also are of relatively complex construction, and are adhesive-bonded together from a large number of components in a cost-intensive manual operation.

Newer irrigation equipment, such as, for example, the Peristeen Anal Irrigation System, made by Coloplast, Denmark, is designed for the specific use requirements of patients who are able to self-irrigate, or to manage and monitor fecal evacuation on their own. The currently available systems are fairly easy to manipulate, but do not address requirements that are essential for the user in practical application.

Moreover, the available irrigation systems for achieving continent phases are designed essentially for the self-care patient. Their use in bedridden, insufficiently cooperative, incontinent patients is largely an impossibility.

The main deficiency is usually the sealing properties with respect to the anus, a problem which in most cases is attributable to insufficiently symmetric expansion of the rectally sealing balloon element. This unreliable geometric expansion is caused by the use of high-volume-expandable balloon materials, such as, for example, latex, silicone or varieties of synthetic rubber, which are mounted as a tubular, non-preformed element on the insertion shaft and expand to a spherical shape when filled under pressure. Belly-like bulges which the balloon envelope acquires during this process, so-called herniations, can be so pronounced that the shaft element becomes displaced into the hernia and is no longer at the center of the balloon. With the shaft and the balloon in such a configuration, it is impossible for the balloon to rest centrally over the anus on the rectal floor, thus resulting in leakage which the patient often is able to alleviate only by continuously manually correcting the position of the catheter shaft in the anus, or that of the balloon in the rectum.

Another problem for patients can be the convenient self-administration of an enema. Available systems, such as, for example, the Persisteen Anal Irrigation System, made by Coloplast, Denmark, function, for example, on the basis of pneumatic delivery of irrigation solution, which can be controlled via a hand pump. Electric pump systems are also used by self-care patients. The usual choice for continuous drainage, however, is a gravity-fed enema system. But there are no systems on the market that meet the manipulation requirements of all irrigation and drainage modalities.

In current systems, the enema catheter is usually removed from the anus by the patient once peristaltic expulsion of the intestinal contents begins. The expelled contents then evacuate more or less abruptly, and can soil the patient or his or her surroundings. However, conventional enema systems, in which the solution is first administered into the colon via a bag and the expelled intestinal contents are then routed back to the same bag, are frequently unable to accommodate the peristaltically moved volume, and leakage, which may include spurting, can occur at the anal inlet element.

In WO 2006/010556 A1, there is described a device of the above species for occluding a natural or artificial anus, the device comprising an inflatable balloon with an approximately toroidal structure, formed from a flat, everted tube section, the two ends of which extend approximately coaxially one inside the other and are (each) joined to a cuff, wherein the outer layer of the everted tube section is provided with a radially enlarged, patient-proximal region for insertion into the rectum (intrarectal region) and has a patient-distal region that is tapered relative thereto and that remains, at least regionally, outside the rectum (transanal region) during use. The transanal portion is constructed of two concentric layers of film, and the concentric tubular films may be lastingly structurally joined to each other by spot connections. However, the compartment thus defined between the layers communicates freely with the lumen of the intrarectal anchor balloon. Both spaces are filled via a single supply line. This has the consequence that due to constant pressure equalization between the two regions, the volume of one region cannot be influenced specifically, which can, for example, detract from the anchoring effect of the intrarectal region.

SUMMARY OF THE INVENTION

The problem initiating the invention herein presented accordingly resides in eliminating the described disadvantages associated with the use of conventional systems for sealing, or occluding, the colon and/or rectum, and, where applicable, for continuous stool drainage and/or for intermittent, large-volume colorectal irrigation.

The solution to this problem is achieved by the fact that in a device of the above species, the intrarectal balloon portion has no functional or spatial connection to the transanal balloon portion.

Although, in the present invention, the transanal segment could also wholly or partially protrude from the proximally or distally directed extensions of the intrarectal anchor balloon, both segments, the intrarectal and the transanal, are structurally and functionally, and, in particular, spatially, separated from each other, and do not communicate with each other, and can, if necessary, be filled and/or emptied separately from each other.

Since, in contrast to WO 2006/010556 A1, in the present invention the intrarectal balloon portion has no functional or spatial connection, or any other communicating connection to the transanal segment, there is no displacement of the filling fluid, or fluids, between the two regions. The two regions, therefore, have considerably enhanced dimensional stability. If necessary, for example, the pressure, and/or the filling volume, in one of the two compartments could be varied independently of the status of the other.

In the design of the anorectal sealing balloon element, the invention preferably abandons the use of highly volume-expandable materials, whose geometry becomes unreliable as they expand from a smaller-dimensioned basic state to the working state. Silicone, as the base material in clinical use heretofore, is preferably replaced by materials of lower volume expandability (compliance), such as, for example, polyurethane (PUR). Particularly in the design of the rectally sealing balloon elements, fully preshaped, thin-walled balloon structures made of, for example, polyurethane (PUR), or materials with similar elasticity and strength properties, are preferably used. The invention utilizes the option of fully dimensional, particularly three-dimensional, preshaping of the film elements to their working size, and the possibility of structurally detailed preshaping of PUR balloon films by the blow molding process. The option, afforded by PUR, of preshaping extremely thin-walled balloon bodies completely and in a structurally detailed manner by blow molding, besides yielding superior functionality with respect to anchoring and sealing, is also intended to contribute to economical production and assembly of the drainage and/or irrigation device. Above all, this option is intended to reduce the number of components needed to construct the head unit of the device, which will be disposed in or near the patient. Assembly, and the durable, particularly mechanical connection of the components, is simplified and its cost reduced by having the individual elements be mateable, for the most part, and lock or snap together. The described assembly options build on the special membrane-like mechanical properties of extremely thin-walled balloon films. Furthermore, the invention introduces particularly functionally advantageous individual components, or segment configurations, which provide an advantage over the prior art in terms of long-term tissue tolerance, anchoring efficiency, continuous sealing performance, and sealing against thin stool or large-volume enemas.

In contrast to conventional systems, in which the sealing balloon element is based on volume-expandable materials, such as silicone or latex, the invention preferably uses polyurethane (PUR), or a material with similar technical elasticity and strength properties, as the base material for the balloon.

The invention further provides that both the intrarectal and the transanal drainage parts are preferably made from PUR. Both drainage parts are made from a single, permeable balloon element, fully inverted into itself. The distally directed end of the preshaped balloon blank is tucked into the lumen of the intrarectal balloon segment and is advanced in the lumen of the proximately directed balloon end all the way to the end thereof. The two ends of the balloon are fixed, parallel to each other, at approximately the same level, on a preanally disposed connector element. In addition, in the inwardly everted, assembled state, the intrarectal anchor balloon comprises a muscle-compartment-like preformation for receiving a separately fabricated funnel element.

In some embodiments, the invention comprises a transanal compartment based on concentric tube elements to which a filling medium can be admitted. This compartment is, however, separated from the intrarectal balloon. The two compartments are filled separately and represent functionally independent units.

The separation of the two segments is preferably effected according to the invention by lastingly, tightly sealing the envelope of the intrarectal balloon segment on, or by means of, a funnel element. It can also, however, be accomplished in the region of the proximal end of the intrarectal balloon by directly connecting the balloon envelope to the surface of portions of the transanal segment.

In addition, the invention is not limited to the transanal portion of the device as exclusively two-layered, but also includes single-layered variants of this segment.

Also described as variant embodiments are configurations of the transanal segment that have, in addition to a one or two-layered tube layer, an additional functional element intended primarily to counteract axial twisting, or twisting-induced occlusion, of that portion.

Whereas in WO 2006/010556 A1, temporary occlusion of the drainage lumen can be produced by means of an occlusion balloon that unfolds in the intrarectal funnel, with the present invention such occlusion is possible in the region of the transanal drainage portion. Not only is the drainage lumen occluded in this case, but sealing with respect to the anal canal is also accomplished by means of the segment that undergoes additional radial expansion when filled.

The intrarectal balloon segment also presented in WO 2006/010556, and which is also completely or optionally residually dimensioned, is included in the invention, as well. In the present invention, this segment is preferably filled in practice with a defined volume that is deliberately chosen to be smaller than the volume of the freely unfolded (filled, but unpressurized), completely preshaped balloon. The intrarectal balloon segment thus lies on the rectal floor as a limp, only partially filled balloon body. It dynamically conforms to the particular morphology, its envelope folding in on all sides. It can thus be put in place for long periods of time with the least possible force acting on the rectal tissue, hence with little likelihood of causing tissue injury. The filling pressure necessary for the drainage system to achieve a sufficient anchoring function in the rectum can ideally be no greater than the physiological pressure that is present there. In response to an increasing colorectally introduced irrigation volume, the pressure in the balloon synchronously follows that of the column of liquid forming above the balloon. Due to the particular sealing abilities of the membrane-like balloon film used, it is not absolutely necessary for there to be a user-controlled increase in filling pressure during irrigation in order to obtain an adequate seal. This may be needed, however, if the anatomy is particularly problematic.

Whereas in the prior art such a reduction of filling pressure also simultaneously determines the unfolding characteristics, and thus the drainage characteristics, of the transanal segment, this is not the case according to the present invention. The two compartments can be regulated separately with regard to the development of the force they exert on the tissues with which they are in contact.

If an axially or proximally directed pulling force is exerted on such a completely preshaped, only partially filled balloon, regardless of whether it is preformed residually beyond the assumable rectal dimensions, or whether in the freely unfolded state, it assumes a size that is smaller than the rectal space to be filled, according to the principle that action=reaction, a balloon filling pressure develops that exactly corresponds to the force acting on the anchor balloon from the proximal direction. If the particular pulling force subsides, the anchor balloon reverts to its low initial pressure. The initially introduced filling volume can, for example, amount to 70-80% of the freely unfolded, preformed volume, and can thus be introduced into the balloon by the user via the filling line all at once, as a single injection of filling fluid.

The use of non- or only slightly volume-expandable materials, such as, for example, PUR having the specification Pellethane 2363 80A, Dow Chemical Corp., ensures that in the presence of an applied pulling action and a resultant increase in filling pressure, the anchor balloon will assume the geometry and dimension it took on during production, but that due to its limited compliance resulting from its constituent material, the dimension cannot be deformed to such an extent that the balloon spreads out distally in a teardrop shape and ultimately slips through the anal opening, as would be expected with high-volume-expandable materials, such as silicone or latex, for example, and is, in fact, observed in routine practice.

According to the invention, the transanal segment is preferably constituted by the extended ends of the intrarectal balloon, but can also be fabricated from separately made tube elements, or from one separately made tube element, each firmly connected to the intrarectal balloon at the ends thereof. The tube ends are optionally connected to an additional pipe- or tube-like element, or lastingly mounted thereon. This element can optionally be extended into the intrarectal segment and there form a funnel-like shape to collect and channel the stool. Even if, in this arrangement, the transanal segment is implemented as double- or triple-walled, it still does not form a commonly tillable compartment with the intrarectal segment.

To stabilize the transanal segment, it is also possible to incorporate a pipe element that preferably continuously connects the funnel element to the connecting element. To prevent lumen-constricting twisting of the transanal segment, the latter is preferably implemented as an elastically self-straightening tube element, or as a radially deformable, self-opening basket weave that conforms with moderate stress to the anal canal.

If the transanal segment is provided with a double-walled implementation, the chamber formed between the funnel element and the connector element can, via a corresponding supply line from outside the patient, either be evacuated or filled with a filling medium, preferably air.

If the space between the two concentric tube layers is evacuated, they come to lie snugly against each other and, being mutually inseparable, constitute a single layer. The central drainage lumen is then maximally open.

If the space between the concentric tube layers is filled, the two layers separate in such a way that the inner layer unfolds into the drainage lumen and sealingly occludes it. The outer layer, on the other hand, expands radially to the wall of the anal canal and thus causes it to be sealed.

The filling and unfolding of the transanal segment in the described manner is particularly advantageous for large-volume colorectal irrigation, with the goal of injecting the largest possible irrigation volume into the intestine, reaching the upper portions of the colon, and simultaneously to prevent the irrigation solution from escaping through the drainage lumen or the anus, past the transanal drainage segment.

The sealing efficiency obtained with the administration of a large-volume enema is improved by the use of completely preshaped, membrane-like balloon films, which optimally adapt to the individual rectal anatomy under the lowest possible filling pressure.

In addition, an option for additional sealing above the transanal segment is provided to keep irrigation fluid from leaking out during the irrigation process.

The invention further describes the efficient collection and drainage of stool-laden and irrigation fluid via a large-lumened drainage lumen, which leads through an intrarectal funnel element within the intrarectal sealing balloon and debouches directly into a bag-type container via a large-lumened tube element connected to the funnel and extending all the way through the anal canal.

The irrigation fluid, and the fractions of formed stool it contains, can thus be discharged even in the case of bedridden or insufficiently cooperative patients, without first removing the enema device from the rectum, the device indwelling intrarectally, independently of a toilet or other suitable amenity to receive the stool.

Due to the particular, largely atraumatic characteristics of the balloon films used for the intrarectal or transanal portions of the device, the enema element can also remain in the patient for prolonged periods and need not necessarily be removed after each use.

The device indwelling in the patient can perform a rectal-anal sealing function during the intervals between enemas. For this purpose, the catheter can be fluid-tightly but gas-permeably sealed at its proximal end, outside the anus. If a bag-type element is connected at the proximal end, rectal secretions, or stool, can also be drained during this interval.

Also provided are collection containers, which are advantageous for use in immobile or uncooperative patients, and which make the intake of irrigation fluid, delivery into the patient, and drainage easier on the patient.

The invention further provides a delivery system for administering the irrigation fluid, which system is adapted to the particular capabilities of the patient.

The inflow of irrigation fluid can be gravity-driven, for example. In this case, the therapist or the patient places a defined volume of irrigation solution at a suitably high level over the inflow point. Intake occurs spontaneously.

As the driving force for the enema, it is also possible to envisage a cuff-like device of the kind used, for example, for pressure-driven rapid intravascular infusion. In this case, a bag-like container holding irrigation solution is inserted into the open central lumen of a cuff to which compressed air can be admitted, and, as the filling pressure in the cuff increases, is squeezed out, or emptied, into the patient. The required pressure is usually generated with a hand pump. Besides a gaseous medium for pressurizing the cuff, fluid media may also be contemplated.

Vacuum drive by means of a water jet pump may also be envisaged. In this case, the bag holding the irrigation solution is fully encased in a bag that is exposed to a vacuum, which can be generated, for example, at a water faucet through the use of a water jet pump.

In addition to continuous drainage of stool from the rectum of a patient, it is also conceivable to employ the head unit described in the invention, consisting of the intrarectal anchor balloon and the transanal segment, for intermittent use in incontinent or only limitedly cooperative patients.

Known enema devices, such as, for example, the system Peristeen Anal, manufactured by Coloplast, Denmark, include rectally sealing balloon components, mounted on a catheter shaft and elastically inflated to their working size. The relatively small lumen of the enema catheter does allow the rapid inflow of irrigation fluid, but generally does not permit the free outflow of irrigation fluid laden with stool particles. The catheter must therefore be withdrawn when peristalsis sets in, and the enema is then voided per via naturalis.

It would be desirable, however, to be able to administer an enema and have evacuation occur problem-free via the rectally placed catheter. This would be advantageous, for example, in bedridden patients, who can be irrigated conveniently and hygienically while lying in bed, and brought to a continent phase. The transanal drainage lumen described herein, with its diameter of up to 3 cm, allows even formed fractions of stool to pass freely.

The previously described embodiments of the head units of the drainage device all lend themselves to use in this context. Instead of the drainage tube, a bag-like, preferably small-volume collecting collection container can be hooked up to the connector directly or via a short tube adaptor.

Due to the large drainage lumen, it is conceivable to perform return flow enemas, in which the irrigation volume oscillates between the bag and the patient.

Alternatively, in self-treating patients who void on the toilet, a short, nozzle-like tube, or tubular film, can be attached for purposes of drainage into the toilet bowl.

The two ends of the everted tube section can extend coaxially one inside the other and possibly (each) be connected to a cuff; in a preferred embodiment of the invention, however, this is not the case.

BRIEF DESCRIPTION OF THE DRAWINGS

Additional features, characteristics, advantages and effects based on the invention will emerge from the following description of various embodiments of the invention, and by reference to the drawings wherein

FIG. 1a (a) is an elevational view of an exemplary preshaping of a balloon blank;

FIG. 1a (b) is a longitudinal sectional view of the everted balloon blank of FIG. 1a (a);

FIG. 1b (a) is a longitudinal section through a first embodiment of a funnel element for insertion into a balloon;

FIG. 1b (b) is a longitudinal half-section through a second embodiment of a funnel element inserted into a balloon;

FIG. 1b (c) is a longitudinal half-section through a third preformation of a funnel element inserted into a balloon envelope;

FIG. 1b (d) is a longitudinal half-section through a fourth preformation of a funnel element inserted into a balloon envelope;

FIG. 1d (b) is a longitudinal half-section through the funnel element according to FIG. 1d (a), partially disassembled;

FIG. 4 illustrates an alternative embodiment of the invention in which the transanal segment comprises two concentric tube layers;

FIG. 5 illustrates a further alternative embodiment of the invention, which combines the embodiment according to FIG. 4 with the elastically deformable, self-straightening and self-orienting tubular basket weave illustrated in FIG. 3;

FIG. 6b (a) is a longitudinal half-section view through a balloon envelope along line VIBA of FIG. 6b (b), with the integration of a filling tube leading to the intrarectal segment;

FIG. 6b (b) is a horizontal section view through a transanal segment of a balloon along line VIBB of FIG. 6b (a), with the integration of a filling tube leading to the intrarectal segment;

FIG. 6c (a) is a longitudinal half-section view through a balloon envelope along line VICA of FIG. 6c (b), with feed from an irrigation tube to the funnel element;

FIG. 6c (b) is a horizontal section view through a transanal segement of a balloon along line VICB of FIG. 6c (a), with feed from an irrigation tube to the funnel element;

FIG. 8a is a diagrammatical showing of an alternative embodiment of the transanal segment;

FIG. 8b is a perspective view of a tube element for stiffening the transanal segment;

FIG. 8c is a perspective view of an alternative tube element for stiffening the transanal segment;

FIG. 9 is a diagrammatical view of an alternative embodiment of the head unit;

FIG. 11a (a) is a longitudinal section through a single, continuous support body, onto which a two-chambered balloon is adapted to be mounted;

FIG. 11a (b) is a longitudinal half-section through another single, continuous support body, onto which a two-chambered balloon is adapted to be mounted;

FIG. 11a (c) is a diagrammatic half-section through a still further embodiment of the invention, wherein a two-chambered balloon is mounted on a single, continuous support body;

FIG. 12a is a diagrammatic illustration of an embodiment of the invention in which a single-chambered balloon is mounted on a single, continuous support body;

FIG. 12b is a diagrammatic illustration of an alternative embodiment of the invention, in which a single-chambered balloon is mounted on a single, continuous support body;

FIG. 13b is similar to FIG. 13a, but with a collection bag portion illustrated in cutaway;

FIG. 13c is a partly sectional, partly perspective view illustrating a cut through a connection between the collection bag and the feeding tube in FIG. 13b;

FIG. 14a is a diagrammatic side view of a preferred embodiment of a collection bag combined with an irrigation apparatus;

FIG. 14b is a generally perspective view of the collection bag of FIG. 14a;

FIG. 14c is a plan view of a cross-section through the collection bag of FIG. 14b;

DESCRIPTION OF THE PREFERRED EMBODIMENTS

Figure 1:
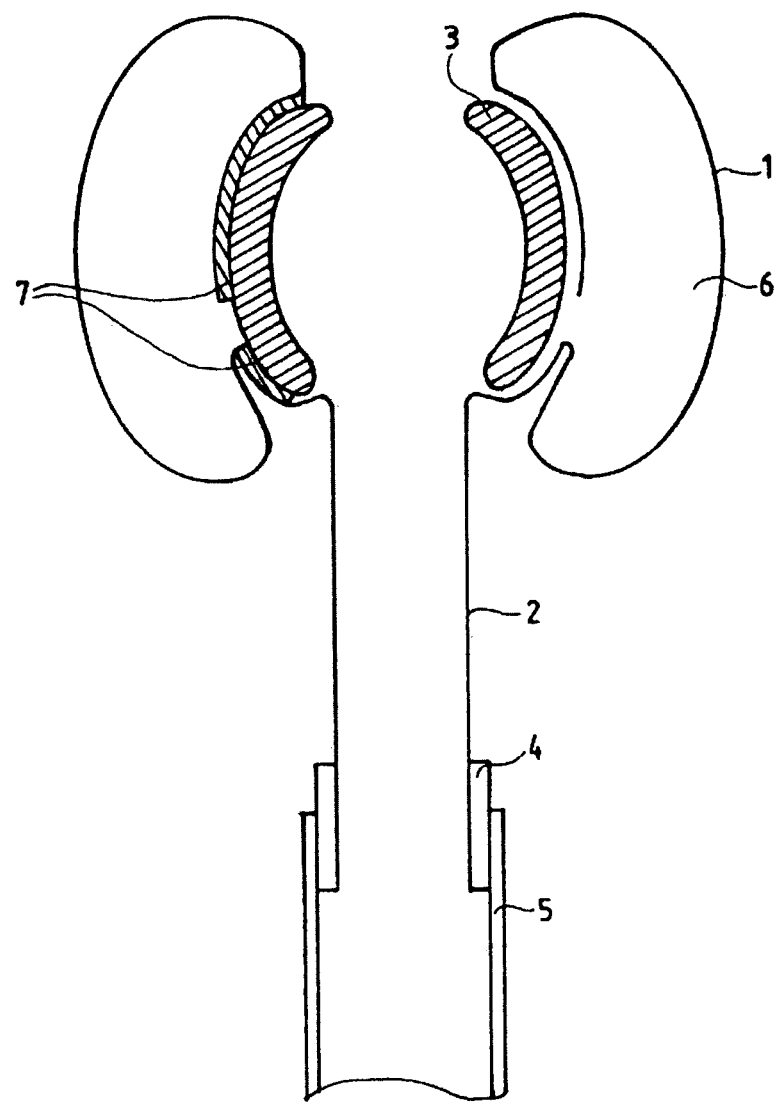
FIG. 1 is a diagrammatic illustration of a simplest embodiment of the head unit of a device according to the invention.

Intrarectal anchor balloon segment 1 and transanal intermediate segment 2 are made from a single, common tube blank 8, the transanal segment 2 of the preshaped balloon film 8 having only a single-layered wall. Intrarectal and transanal segments 1, 2 of the balloon film 8 form a structural unit in the illustrated variant of the device, but present no functional separation in the state of being assembled and fixed on/against a funnel. As FIG. 1 shows, the tube blank 8 is tucked back into itself in the region of the intrarectal anchor balloon 1, particularly inwardly, or in such a way that any gap remaining between the end edge of the everted tube blank 8 and a middle tube section facing the end edge is inside the intrarectal anchor balloon 1; as a result of the eversion, the intrarectal anchor balloon 1 exhibits essentially a toroidal structure.

The two segments 1, 2 of the tube 8 are segregatingly, or sealingly, separated from each other by an approximately rotationally symmetrical element, a funnel element 3, which is inserted from the distal direction into the inner, central hollow of the anchor balloon 1. The body of the funnel element 3 covers any gap that may remain on the inside of the intrarectal anchor balloon 1 between the end edge of the everted tube 8 and a middle tube section facing the end edge. By durable, firm connection of the anchor balloon envelope 1 to the funnel element 3, a compartment 6 is created which is closed, or sealed, in the region of a remaining gap on the balloon tube envelope 8, and is therefore tillable with a fluid, and which extends in, like a cuff, around the lateral or radially outlying portions of the funnel element 3, and thus unfolds during filling. The connection can be simplified, or improved, by specially configured preformations 7 of the funnel surface and/or of the balloon tube 8, which preformations will be described in more detail hereinbelow.

The transanal segment 2 is followed in the proximal direction by a connecting element 4, which terminates the head unit and forms the transition to a drainage tube 5.

The preshaped balloon tube 8 comprises a medially disposed region 9 which is preshaped into an approximately outwardly spherical form, and which in the assembled state forms the radially outwardly disposed envelope of the intrarectal anchor balloon I. An extension 10 extending proximally from the sphere 9 is provided with a cylindrical shape and corresponds, in the assembled product, to the transanal segment 2 of the head unit. An oppositely directed extension is configured as a funnel encasing compartment 11 for receiving the funnel element 3, analogously to the encasement of a muscle group by fascia in a muscle compartment. Joined to each end are portions of a tube blank 12 used in the blow molding process. To fabricate the head unit illustrated in FIG. 1, the balloon blank can, for example, be tapered in section planes 13, as can be understood from FIG. 1a.

FIG. 1a (b), the right-hand drawing, further shows how a balloon-blank region forming the funnel encasing compartment 11 is tucked back into the interior of the intrarectal sphere 9, and how, in a subsequent step, the funnel element 3 can be inserted, or mated, into the now-inverted encasing compartment region 11.

The inner contour of the inverted encasing compartment region 11 here corresponds, preferably with an exact fit, to the outer contour of the funnel element 3 inserted into the intrarectal balloon segment 1. Encasing compartment 11 can be preshaped, or dimensioned either to almost fully embrace, or to only partially embrace, the periphery of the funnel element 3 it receives.

FIGS. 1b (a) to 1b (d) show various preformations of the balloon tube 8 and of the funnel element 3, which, respectively or chiefly in combination, facilitate convenient assembly, twist-free longitudinal axial straightening, and durable, sealing interconnection of the balloon tube 8 and the funnel element 3:

Those portions of the intrarectal and/or transanal balloon segment 1, 2 that are in permanent areal contact with the funnel element 3 in the final assembled state are preferably sized to be slightly smaller than the corresponding structures of the funnel element 3 that are in contact with the balloon tube 8. In this way it can be ensured that in the assembled state, the balloon tube 8 conforms to the funnel element 3 on all sides with slight stretching and with no folds. Funnel element 3 and encasing compartment 11 are preferably shaped geometrically in such a way that the funnel 3 virtually snaps into its mounted position when inserted into the encasing compartment 11. The outer contour of the funnel 3 can be given, for this purpose, a suitable three-dimensional basic shape such as, for example, that of an olive, a sphere or a barbell; the inner contour of the encasing compartment 11 is shaped as a counterpart thereto. Preferably, the outer contour of the funnel element 3 is doubly convexly curved, i.e., in both the axial direction and the azimuthal direction, in at least one region, and it is preferably doubly convexly curved in its entirety, i.e., over the entire region of the outer contour. Corresponding thereto is an inner contour of the funnel encasing compartment 11, which is at least regionally doubly concavely curved, i.e., in both the axial and the azimuthal direction; preferably, the entire region in contact with the funnel element 3 is doubly concavely curved.

FIG. 1b (a) shows that, to further simplify the assembly of the thin-walled balloon films 8, the surface of the funnel element 3 can be provided with special annular protrusions 14, which extend circularly about the surface of the funnel, and which increase their contact stress in the region of contact with the balloon tube 8, and thus have a quasi-sealing effect. Such sealing or delimiting structures are advantageous, especially when the balloon tube 8, in the tightly filled state, is placed on a shaft base, there moved into the mounted position, and untwisted and straightened out along the longitudinal axis. The targeted placement of glue, or solvent, between a shaft element and/or the funnel element 3, on the one hand, and the balloon tube 8, on the other, particularly in a limited and/or defined region, can also be improved in this way. FIG. 1b (b) shows that, for example, an adhesive can, in a spatially limited manner, be placed in, particularly injected into, a gap 15 located behind the protrusion 14 and between the funnel 3, on the one hand, and a region 16 of the balloon film 8 that is in contact with the funnel 3, on the other, without any risk of this adhesive straying into the region on the other side of the annular protrusion 14.

FIG. 1b (c) shows that, to further simplify the positioning and, above all, the axial straightening and fixation of the film, the convex protrusion 14 extending annularly, or circularly, about the periphery of the surface of the funnel element 3 can be improved by providing the adjacent balloon envelope with a corresponding concave preformation 17 that is approximately complementary to the protrusion 14. This permits a further interlock effect in positioning the film on the funnel. The film 8 is as if rail-guided in its movement, without deviating from being precisely positioned on the underlying element, i.e., the protrusion 14, and can be conveniently untwisted along the balloon's longitudinal axis and straightened out along the longitudinal axis.

In addition, an interspace 18 receiving a medium, e.g. adhesive, that lastingly bonds the structures together can be provided between the funnel element 3 and the balloon tube 8, preferably in the region of their preformations, particularly in the apical contact region of the preformations. Correspondingly, the controlled distribution of an adhesive medium between the balloon film and the funnel surface can be accomplished by means of a groove 19 running apically on the annular protrusion 14. The adhesive bonding medium can be conveyed to the area from the funnel lumen and fed in via a conduit-like preformation 20, which can be seen in FIG. 1*b* (d).

The invention further provides that the funnel element 3 and the balloon tube 8, are connected to each other by welding, preferably in the region of at least one convex preformation extending annularly and/or circularly about the periphery of the funnel. Due to the thus locally obtained increase in the contact stress of the tube 8 on the substrate, this is advantageous for welding the two structures together, since a suitable thermal welding tool can be positioned there and create a reliably fold-free joint between the surfaces.

Figure 1C:
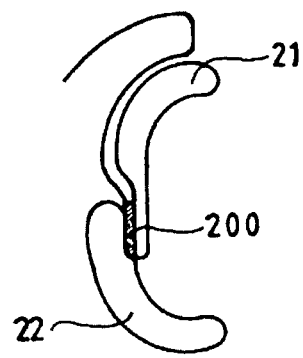
FIG. 1c is a longitudinal half-section through a two- or multi-component implementation of a funnel element.

As FIG. 1*c* shows, the funnel element 3 can be composed, for example, of two mateable or otherwise suitably interconnectable parts, for example of annular parts 21, 22 disposed one behind the other in the axial direction. During assembly, the parts 21, 22 are, preferably separately, lastingly connected, for example by gluing, respectively to the distal and the proximal ends of the balloon 1. If the funnel components 21, 22 are—at least regionally—lastingly connected to the balloon film 8, they can then be untwisted over the longitudinal axis of the balloon film 8 and thus, axially straightened, without any twisting of the balloon film 8, permanently sealingly joined together.

The interconnection of the balloon tube 8 and the funnel components 21, 22 can also take place such that the connection points come to be located in the region of the joint between of the funnel components.

For example, the distal end of the balloon 1 can be glued to funnel component 21, particularly in the joint region 200 with the component 22. To accomplish this, the encasing compartment portion 11 of the balloon film 8 is glued, or lastingly joined, to the proximal edge of component 21. Both structures are then inserted together into a congruent receiving structure at the distal edge of the component 22, and, after axial straightening, are also adhesively bonded there.

Figure 1D:
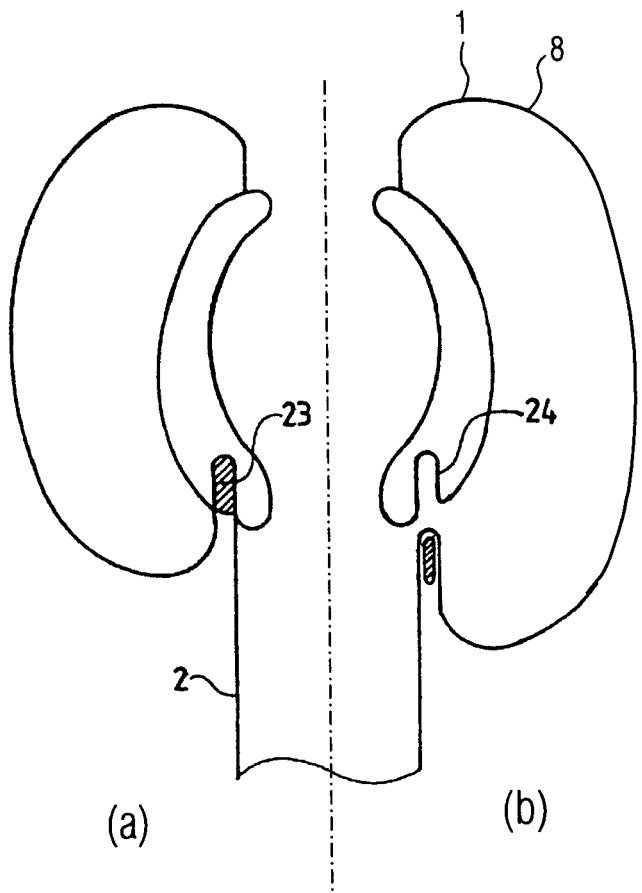
FIG. 1d (a) is a longitudinal half-section through another, entirely assembled funnel element.

In a similar multi-component construction according to FIG. 1*d*, the proximal tight sealing of the balloon tube 8 can be achieved by means of the funnel element 3. This assembly technique is based on a separate ring-shaped element 23. The element 23 can, for example, be advanced from the proximal direction through the transanal segment 2 to the proximal fixing position of the balloon film 8 on the funnel 3, particularly to the transition from intrarectal balloon 1 to transanal segment 2, and there optionally fixed to transanal segment 2 by gluing, welding, or the like. Snap fit placement of the ring element 23 can be achieved by means of a preformation corresponding to the ring element 23 and located at the proximal end of the balloon envelope 1.

The ring element 23, carrying along the thereto-attached distal end of the transanal segment 2, is then mated into a correspondingly preshaped, annular-groove-like preformation 24 at the proximal end of the funnel element 3, and can be fixed there, for example, by adhesive bonding, welding, or the like.

The ring element 23 can exhibit a slightly higher Shore hardness than the rest of the funnel components 21, 22, so that, if the diameter is made to be slightly larger or smaller than that of the receiving preformation, the two funnel components 21, 22 can be snap-locked together under slight stress.

Figure 2:
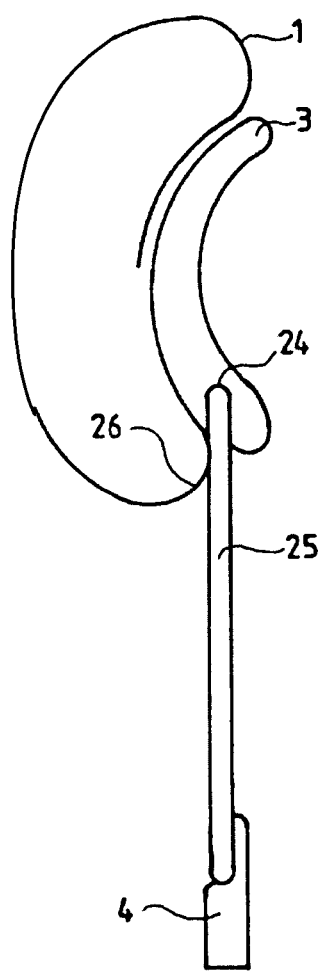
FIG. 2 is a diagrammatic illustration of an alternative embodiment of the invention.

The embodiment of the device shown in FIG. 2 comprises, instead of a proximally extended balloon end arising from the anchor balloon 1, as illustrated, for example, in FIG. 1, a separate, transanally extending, thin-walled pipe piece or tube piece, which continuously connects the funnel element 3 to the preanal connector element 4. This element is fabricated of an elastic material with a high restoring force, so that despite being made as thin-walled as possible, it automatically straightens out, or untwists, when radially deformed, or twisted about its longitudinal axis, and thus spontaneously returns to its low-stress, open-lumened initial state.

The figure shows exemplarily how the joint between the pipe piece and/or tube piece 25 and the funnel element 3 can take the form of a preformed annular groove 24 at the proximal funnel end 26. In this arrangement, the proximal end 26 of the balloon envelope 1 can be laid over, pulled onto, or otherwise guided over, the distal end of the tube piece 25, such that the latter is lastingly sealingly connected to funnel element 3 by the insertion of the distal end of the transanal segment 2 into the annular groove 24.

Figure 3A:
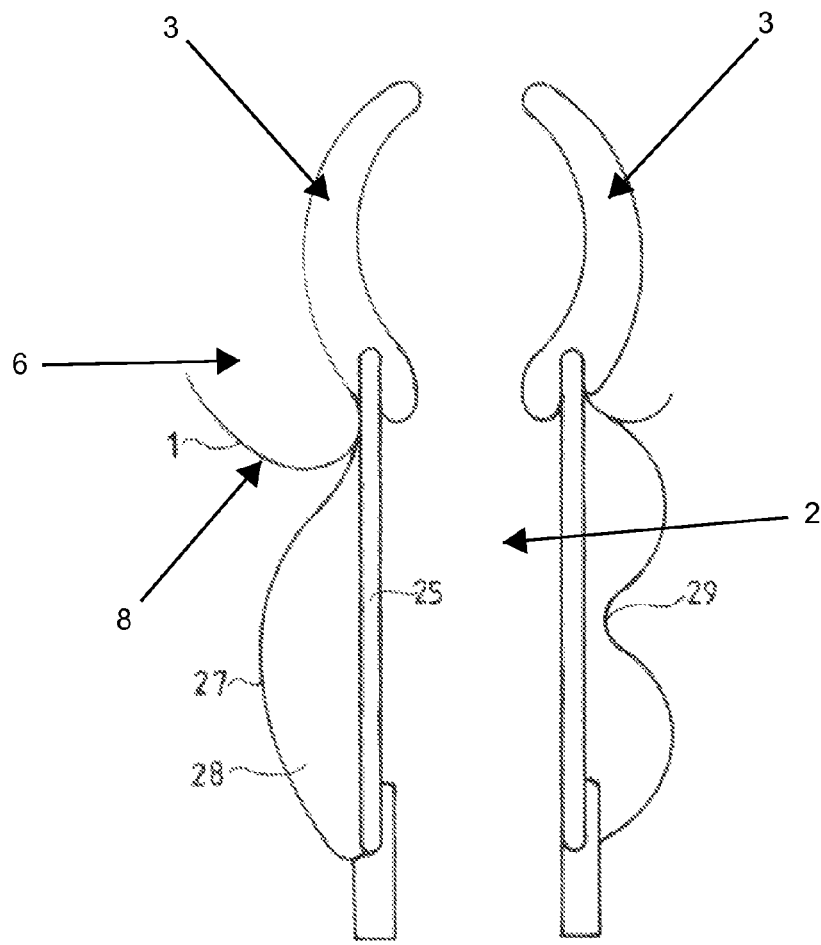
FIG. 3a illustrates a further alternative embodiment of the invention, with a combination of an anchor balloon and a transanal segment protruding from the anchor balloon envelope, as illustrated in FIG. 1, but with a stabilizing pipe piece shown in FIG. 2.

FIG. 3*a* shows a combination of the anchor balloon 1 with the transanal segment 2 arising from the anchor balloon tube 8, as depicted in FIG. 1, with the stabilizing tube piece and/or pipe piece 25 shown in FIG. 2. The transanal segment here forms a separately fillable compartment 28 created between the inwardly disposed pipe piece and/or tube piece 25 and an outer, proximally extended anchor balloon envelope 27. As the compartment 28 is filled, regardless of the volume expandability of the envelope, or the diameter to which it is preshaped during production, the seal with respect to the anus is improved by radial expansion of the balloon envelope 27. Under forced filling, the drainage lumen of the head unit can additionally be constricted toward the center and nearly occluded. Alternatively to preshaping the envelope 27 from the proximal tail of the anchor balloon 1, a separately fabricated balloon body, or tubular film body, can also be used as the envelope 27. The envelope 27 outwardly defining compartment 28 can further be preformed into a barbell or hourglass shape. In such a configuration, a preferably medially disposed waist 29 is preshaped to accommodate the structures of the anal canal. If the transanal compartment 28 is placed under pressure, as occurs, for example, during the instillation of the irrigation fluid, the described preformation 29, on the one hand, serves to securely anchor the head portion of the device and, on the other hand, helps to form a seal against irrigation fluid leaking from the rectum.

The previously described techniques—for example, adhesive bonding, welding, optionally in the region of a preformation, etc.—can be used to fix and tightly seal the components necessary for this embodiment in the region of transition between the intrarectal and the transanal compartments 6, 28.

Analogously, the tubular balloon envelope 27 preferably arising from the anchor balloon 1 can be combined with a radially deformable tubular basket weave 30 that conforms, with light stress, to the transanal contours. In the non-deformed, low-stress, initial state, tubular basket weave 30 has an open lumen of approximately 2-3 cm. The radially directed restoring force exerted on the anus as the lumen constricts is very low and precludes the formation of pressure ulcers. If there is a decrease in the tone of the anal sphincter during the defecation reflex, the tubular basket weave 30 conforms to the then-opening transanal canal, thus facilitating the expulsion of stool. The tubular basket weave 30 preferably continuously connects the intrarectal funnel element 3 to the preanal connector element 4. It is preferably disposed in the interior of the tube segment 8, but can also, alternatively, extend beyond the outer surface thereof. In the radially constricted state 30a, according to FIG. 3c, the basket weave 30, which is preferably constructed of rigid, flexurally deformable filaments, undergoes a marked increase in length, for which allowance is made in a corresponding length specification of the surrounding transanal balloon envelope 27.

The assembly of the component parts is performed by the previously described techniques.

FIG. 4 represents an embodiment whose transanal segment comprises two concentric tube layers 27a and 27b. As previously described, these can be composed of the extended ends of the intrarectal balloon 1. In the preferred embodiment, the inner tube layer 27b arises from the proximal extension of the intrarectal balloon sphere 9. The outer tube layer 27a is preferably configured as a separate, thin-walled tubular film element, which is preshaped so as to be preformedly cylindrical or, alternatively, congruent with the anal canal.

Alternatively, the two layers can be composed of separately fabricated tubular films.

The compartment 28 formed between the two tube layers 27a, 27b can be partially or completely filled with a medium from outside the patient's body, or completely evacuated, via a supply line 31 routed through the connector element 4.

In the evacuated state (corresponding, for instance, to the left half of FIG. 4), the two tube layers 27a, 27b lie firmly one inside the other, and behave virtually as a single-layered wall. In the filled state (corresponding, for instance, to the right half of FIG. 4), the two layers 27a, 27b separate from each other and the compartment 28 is maximally open.

In the tightly filled state, the inner layer 27b expands toward the center of the drainage lumen and occludes it fluid-tightly. The outer layer 27a, by contrast, expands toward the anal wall and conforms to it, also leak-tightly, following the particular anatomy.

Under partial filling, or filling with a few milliliters of fluid medium, the two layers 27a, 27b separate. The two thin-walled films 27a, 27b, supported virtually frictionlessly by the fluid medium, glide freely displaceably with respect to each other. Lesions of the kind known to be caused in the particularly sensitive region of the anal canal by minimally dynamic films that remain in static contact with the tissues can be avoided more effectively by the free interplay and the gliding of the film layers 27a, 27b.

The connection of the component parts or film layers 27a, 27b to the proximal funnel end 26 can be accomplished on the basis of an annular element 23 inserted into the annular preformation 24 at a proximal edge of the funnel element 3. The inner layer 27b can, in this case, be passed over the ring element 23, as illustrated in FIG. 1c, and connected to or snapped together with the funnel element 3. The outer layer 27a can be adhesive-bonded at its distal end to the ring element 23 in a preceding assembly step.

Figure 3B:
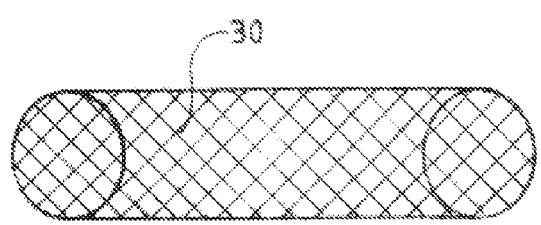
FIG. 3b is a perspective view of a stabilizing pipe piece in its original shape.
Figure 3C:
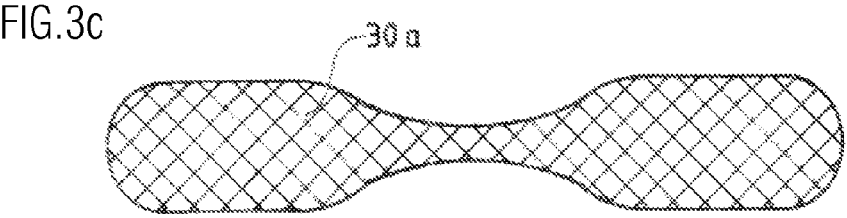
FIG. 3c shows the stabilizing pipe piece according to FIG. 3b, partially deformed.

FIG. 5 combines the previously described embodiment with the elastically deformable, self-straightening and self-orienting tubular basket weave 30 described in FIG. 3. The previously described tube element or pipe element 25 (not shown in FIG. 5) can be used alternatively to the tubular basket weave 30.

The previously described elements 25, 30 are preferably disposed between the two film layers 27a and 27b, thus connecting the funnel element 3 to the connecting element 4.

Figure 6A:
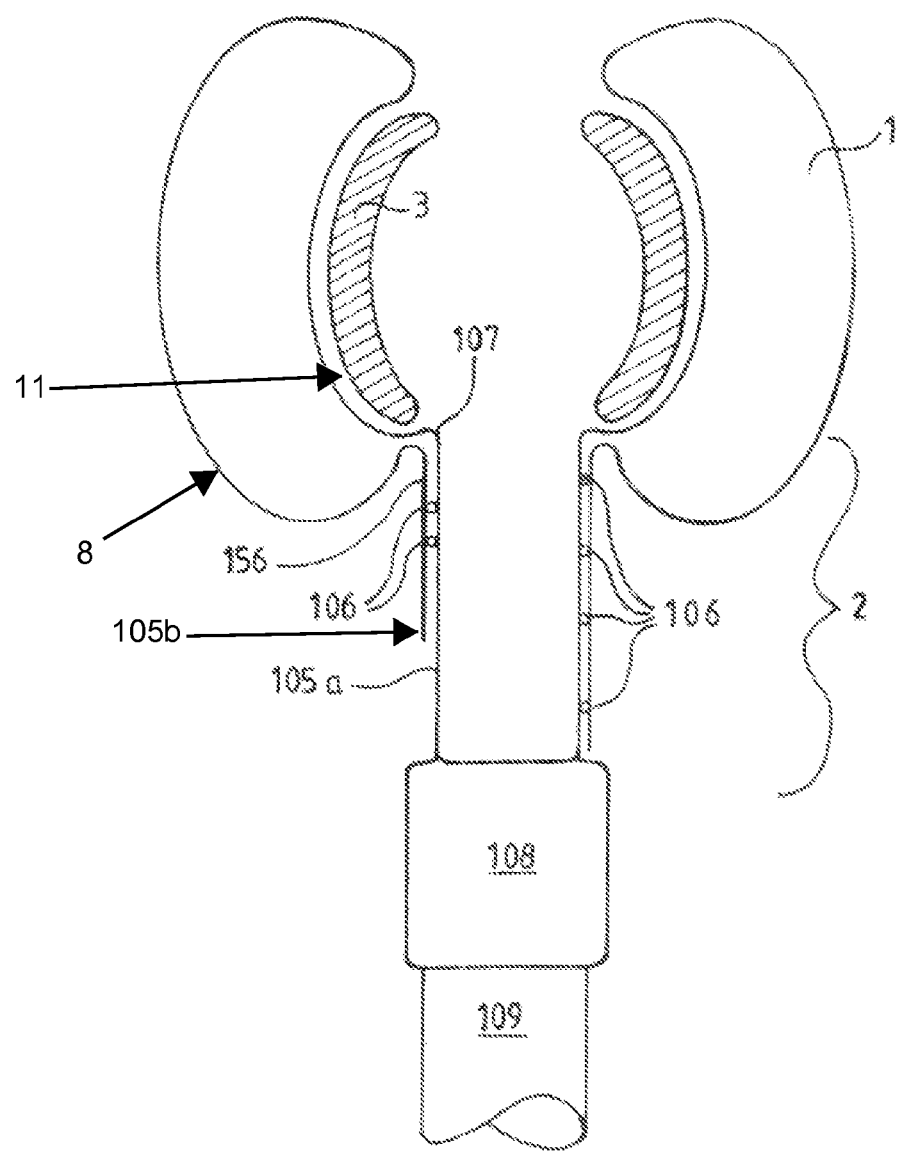
FIG. 6a is a diagrammatic illustration of one embodiment of the head unit according to the invention.

FIG. 6a shows another embodiment of the invention. Here, intrarectal anchor balloon 1 and transanal intermediate segment 2 are made from a single, common, tubular balloon blank 8 that has been completely preshaped in advance, one end 105a of the balloon tube 8 being pulled through its other end 105b. The two ends 105a, 105b lie concentrically against each other in the transanal segment 2 of the device and are preferably lastingly connected to each other in a contact region 106 by an areally acting connection technique. The contact region 106 between the two balloon ends 105a, 105b preferably begins at a bottom edge 107 of the funnel encasing compartment 11, or a few millimeters proximally therefrom. It extends over the partial, or full, length of the transanal segment 2 of the device.

The contact region 106 of the tube ends 105a and 105b is therefore constituted as double-layered. The layers are, of course, preferably continuously firmly connected to each other. Partial chambering in contact region 106, hence a partially areal connection, may be envisaged. But there is no possibility of filling by means of, or connection to, another pressurizable space in any other compartments, except for the environment; in particular, there is no continuous connection of any kind to the compartment 6 inside the intrarectal balloon 1. The preferably continuous double layer of material in the contact region 106 gives the transanal segment 2 higher rigidity and thus—and most important—counteracts axial twisting and the attendant constriction of the drainage lumen. It also guarantees the improved tendency of the segment lumen to straighten out spontaneously.

Although, in the illustrated variant of the device, the intrarectal and the transanal segment 1, 2 of the balloon tube 8 form a structural unit, they are functionally decoupled from each other.

Connected proximally to the transanal segment 2 is a connecting element 108 that forms the transition to a drainage tube 109.

For purposes of filling the intrarectal balloon 1, it is recommended to integrate a filling tube 110 into the contact region 106 between the two tube ends 105a and 105b. In the simplest case, this can be done by interposing the filling tube 110 between the two concentrically disposed film layers or tube ends 105a, 105b, as illustrated in FIGS. 6b (a) and 6b (b). The fixing and sealing can be accomplished by adhesive-bonding or welding together the components 105a, 105b, 110 to be joined.

The task of accommodating the filling tube 110 in the contact position 106 can be simplified by means of suitable, exactly fitted, groove-like preformation(s) 111 disposed in the tube ends 105a and/or 105b, and receiving the interposed filling tube 110, as can be seen on the right in FIG. 6b (b).

To ensure the delivery of irrigation fluid to intrarectal segment 1, it is preferred to integrate an irrigation tube 112, which preferably is disposed inside the drainage lumen 109, or fixed in a corresponding groove-like preformation 113 inside the transanal segment 2, as illustrated in FIGS. 6c (a) and 6c (b).

In intrarectal segment 1 of the device, the irrigation tube 112 can be received and held in the funnel element 3 by a suitably preshaped preformation 114, e.g. by being mated thereonto or thereinto. Preformation 114 can form a debouchment 115 to the drainage tube 109.

Figure 7A:
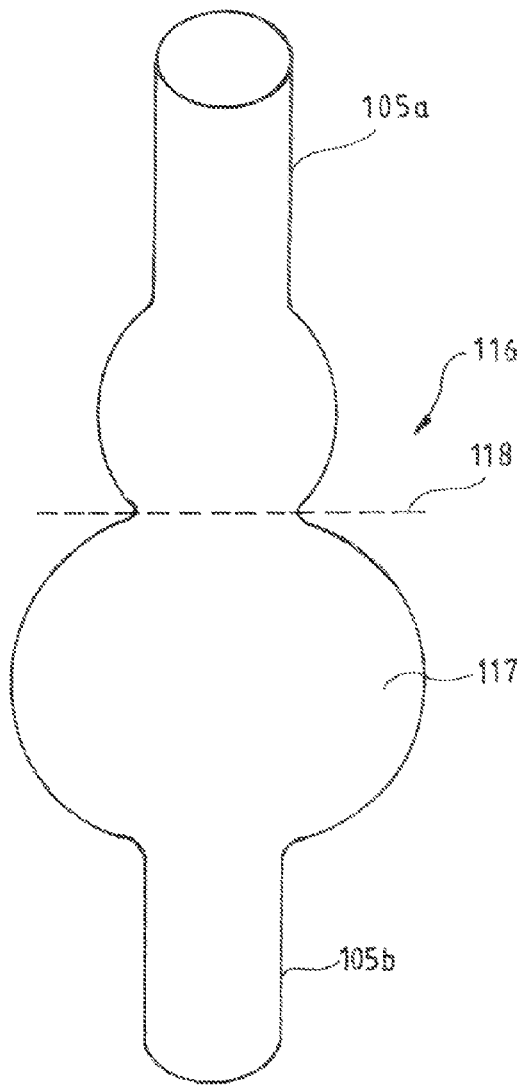
FIG. 7a is a perspective view of an alternative preshaped balloon blank.
Figure 7B:
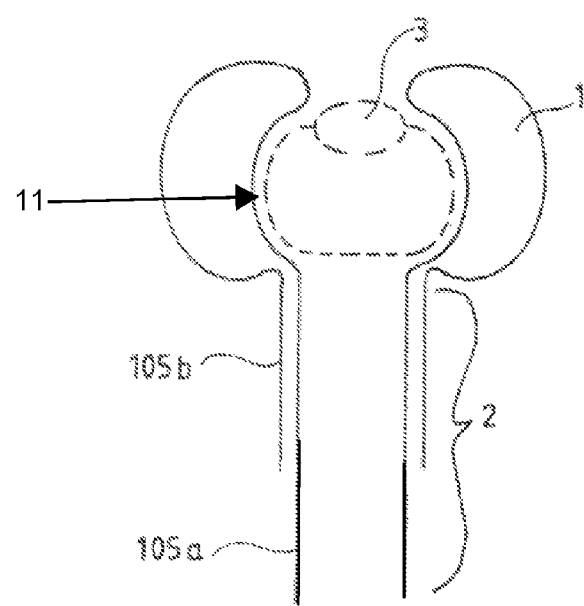
FIG. 7b is a diagrammatical view of the balloon blank of FIG. 7a in everted state.

As can be seen from FIG. 7a, the preshaped balloon blank 116 has a medially disposed spherical formation 117, which in the assembled state constitutes the envelope of the intrarectal anchor balloon 1. Extension 105a of the sphere 117 preferably has an elongated cylindrical shape and corresponds, in the assembled product, to the transanal section 2 of the head unit. During assembly, the end 105a is pulled back through the opposite end 105b, such that a line 118 comes to be the fold-back line, directly at, or near, the distal, patient-internal end of the device, according to FIG. 7b.

Extension 105a can optionally form the funnel encasing compartment 11.

In that case, the inner contour of the inverted encasing compartment 11 corresponds, preferably with an exact fit, to the outer contour of the funnel element 3 inserted into the intrarectal unit.

In the embodiment according to FIG. 8a, the tube ends 105a and 105b are not connected directly to each other, but are instead each connected to the surfaces of a sleeve- or tube-like component 119 disposed between them, the purpose of which is to modify the mechanical properties of the transanal segment 2.

In the ideal case, the transanal segment 2, with or without supplementation of this kind, is so designed mechanically such that without the application of external force, i.e., for example, in the freely unfolded state, transanal segment 2 straightens out by virtue of its elastic force, exhibiting a circular cross section, without entering into contact with the anal canal. Under a slight force acting from the outside, the segment 2 is adapted to collapse, or to undergo deformation, that substantially occludes the lumen.

In addition, a certain degree of protection against twisting in the transanal segment 2 of the device is procured by the choice of a suitable elastic sleeve 119. The elasticity of the sleeve 119 is selected such that after being axially twisted, even in situ, the transanal segment 2 substantially untwists automatically and returns to its low-stress initial state. The sleeve 119 preferably comprises polyurethane with a hardness rating of 30 to 70 A, which material can be manufactured or processed by extrusion, injection molding, casting or dip molding. Alternatively, it is also feasible to use, for example, silicone or a material with similar mechanical or, especially, elastic properties.

The sleeve 119 can either be constructed as uniformly thick-walled throughout, as illustrated by sleeve 119a at the upper right in FIG. 8b, or, for example, as single-turn or multi-turn—where appropriate, counterwound—helical struts or stiffeners 120, as illustrated at the lower right in FIG. 8c. The area between the struts or stiffeners 120 can be preshaped as a thin-walled structure with a thickness of, for example, 0.2 to 0.4 mm, or, in the case of the counterwinding of a plurality of spirally or helically extending struts 120, can also be perforated as if by windows. The preferably helically extending struts 120 can have a diameter of, for example, 0.75 to 2.0 mm.

The sleeve 119 can further consist of an elastic soft foam, for example PUR foam.

Alternatively, the sleeve 119 can be constructed as an elastic, double-walled cylinder, the space between the walls being tightly filled with a compressible or incompressible medium.

Sleeve 119 can be connected to the ends 105a and 105b areally, particularly over the entire area, or a large area, or only a portion thereof. Its length is at least equal to the length of the anal canal, i.e., approximately 3 to 5 cm, but preferably reaches from the funnel element 3 to the connector 4.

Sleeve 119 preferably lies between the ends 105a and 105b; alternatively, however, it can be disposed externally to outer layer 105b, or internally to inner layer 105a.

If placed in the interior of the transanal segment 2, i.e., in the interior of the layer 105a, the sleeve 119 can also, as a further embodiment, arise from the funnel element 3, or be lastingly continuously connected thereto, as can be seen in FIG. 9.

Sleeve 119 preferably is provided with suitable preformations to receive venting lines and irrigation supply lines.

In the case of the sleeve 119 being fixed between the tube ends 105a and 105b, in an alternative embodiment the funnel element 3 and the sleeve 119 constitute a unit 121. To assemble this embodiment, the sleeve 119 is advanced on the tube end 105a to the fold-back line 118 and is areally lastingly connected thereto. End 105b is then rolled back over the unit formed by the sleeve 119 and the inner tube end 105a. End 105b is then fastened to the surface of the transanal sleeve segment 2.

Figure 10A:
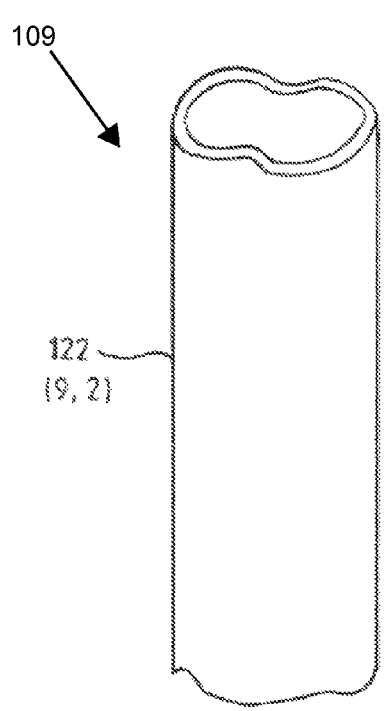
FIG. 10a is a perspective view showing a first manner of compartmentalizing a tube element of the device.
Figure 10B:
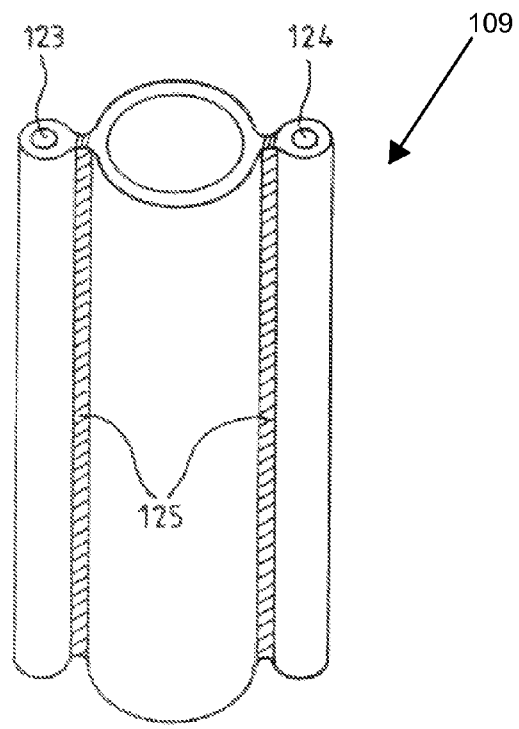
FIG. 10b is a perspective view showing a second manner of compartmentalizing a tube element of the device.

FIGS. 10 (a) and 10 (b) show further options for the design of the transanal segment 2 and stool conveying drainage tube 109.

Here, supply tube compartments, for example of the kind needed to fill the intrarectal balloon 1, or also to deliver irrigation fluid to the intrarectal end, are partitioned off from a base tube 122, or compartmentalized by longitudinally oriented weld seams 125 applied to the base tube 122 of the transanal and/or stool-conveying drainage tube 109. Compartments 123, 124 so created thus form a conduit.

FIGS. 11a (a) to 11a (c) show an embodiment of the invention in which the funnel element 3, transanal tube piece 25, and the connector element 4 comprise a preferably continuous manufactured unit 141.

The three elements 3, 4, 25 of the unit 141 preferably are made from an elastic synthetic material in a common operation. Injection molding, hot molding, dip molding, compression molding or sinter molding are examples of processes that can be used for this purpose. The funnel-like element 3 and the connector 4 are provided in their respective proximal portions, preferably while being formed in the mold, with punctures 145 to permit the assembly-facilitating leadthrough, or the attachment of incoming tube connections, such as, for example, an irrigation line 146 or a filling line 147 serving the intrarectal compartment 6.

Unit 141 is made, for example, from polyurethane with a hardness between 80A to 60D, and is preferably implemented with a consistent material wall thickness of 0.2 to 0.4 mm. If polyurethanes with a hardness rating of 30A to 70A are used, the wall thickness can be increased to up to 1.0 mm.

An important factor to consider in seeking the best functional match between wall thickness and material hardness is the self-straightening of the unit 141 under an externally applied deforming force. In the ideal case, the inner lumen of the unit 141 is circular in cross section when no external force is being applied. Under a force equivalent to a water column 15 to 25 cm high, but preferably 5 to 15 cm high, pressing uniformly and on all sides of a 3 cm central section of the segment, the segment walls will collapse and occlude the lumen, as a result of which opposite portions of the wall should come at least into direct partial contact, that is, should touch one another.

Spontaneous straightening should also be achieved in the basic state when the unit 141 is twisted about its longitudinal axis; that is, spontaneous straightening should be promoted in the transanal position.

FIG. 11a (c), bottom, elucidates attachment points 151 of the two-chambered balloon body 1, 2 to the unit 141 serving as a continuous support, and indicates the balloon shape that develops in the presence of such a fixing arrangement when the compartments 6, 28 so created are filled.

Figure 11B:
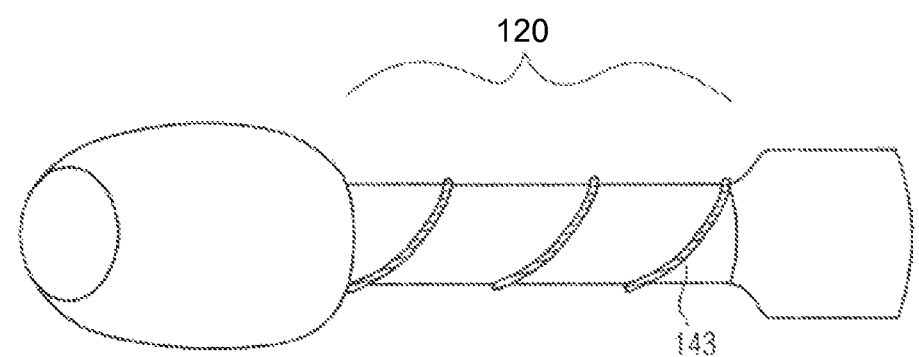
FIG. 11b is a perspective view of an alternative embodiment of the invention, in which a two-chambered balloon is mounted on a single, continuous support body.
Figure 11C:
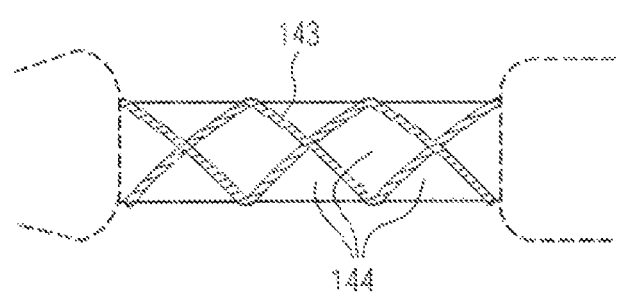
FIG. 11c is an elevational view of a transanal portion of the embodiment according to FIG. 11a (a), in which a two-chambered balloon is mounted on a single, continuous support body.

FIG. 11*b* shows an embodiment with lumen-occluding deformability of the stiffening segment 120 by helical struts 143 which extend over the inner or outer surface of segment 120, and which can be arranged as a plurality of parallel turns running in the same direction at a given angular offset. The struts 143 can also be mounted as one or more turns running (mutually offset) in opposite directions, like at FIG. 11*c*. The resulting mesh-like structure can be provided, in its regions 144 located between the struts 143, with thin-walled areas that can be reduced to wall thicknesses of as little as 0.1 mm.

In a casting operation, the struts 143 further serve to ensure a sufficiently rapid flow of plastic compound into the mold, if the described very thin-walled regions 144 are to be pre-shaped successfully in advance.

FIG. 12*a* shows the previously described continuous base body unit 141 combined with a balloon element 1 that forms only a single fillable intrarectal compartment 6. The balloon 1 sits against the attachment points 151, which extend circularly about the periphery of the funnel element 3. A second transanal balloon segment is not provided in this case.

FIG. 12*b* shows an embodiment with a unit 141 on which is mounted only a transanal balloon component 148 with a compartment 149, there being no intrarectal balloon component.

The transanal balloon component 148 can preferably be fashioned in an hourglass shape, to enable it to conform optimally to the contours of the anal canal in situ, so as to provide better anchoring. Correlatively, a balloonless, funnel-shaped olive 152 can have a correspondingly increased diameter and can present a large enough outer contact face 153 to anchor the device sufficiently well in the rectum.

Figure 13A:
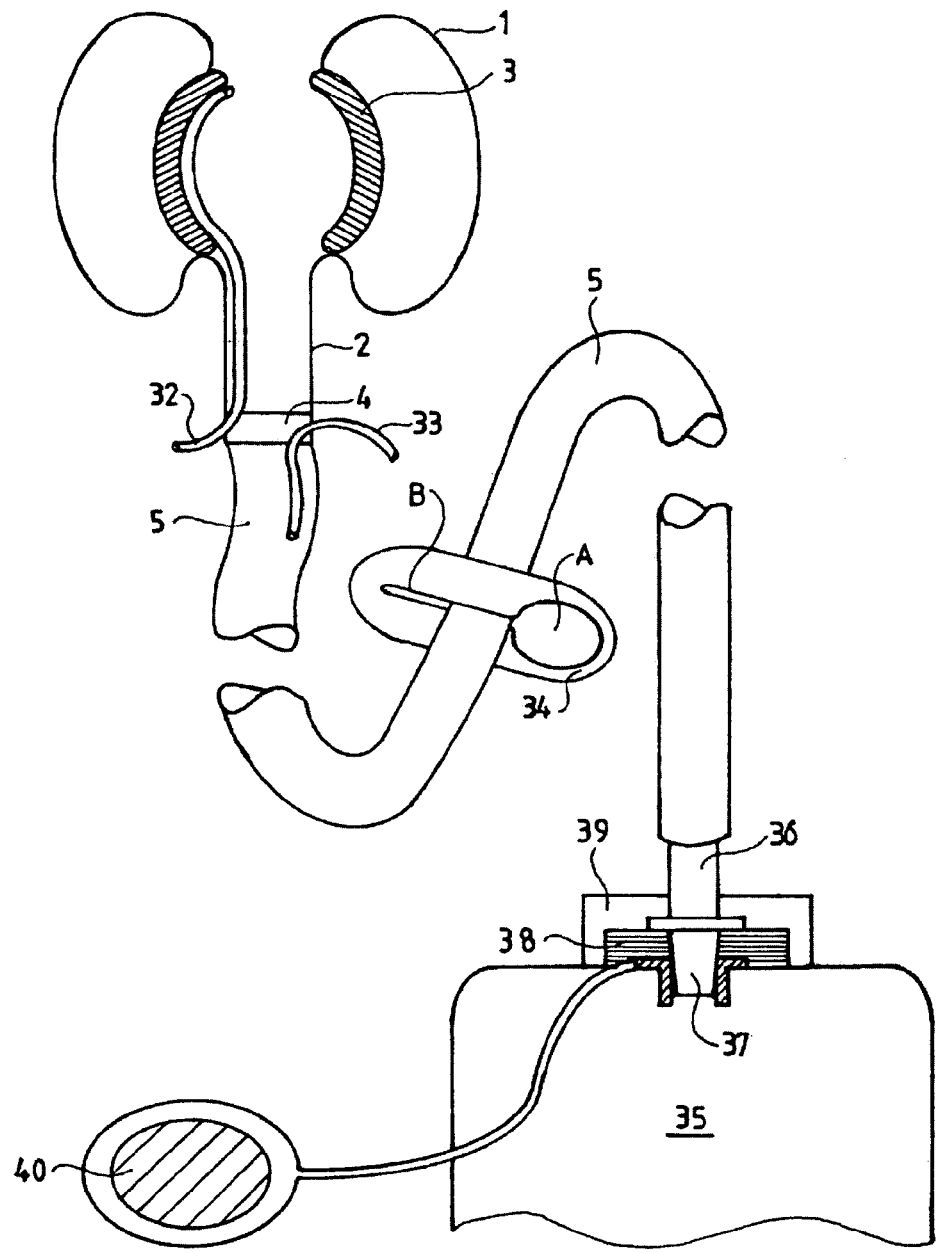
FIG. 13a is a diagrammatic illustration of the entire device according to the invention, including substantially all components.

The individual components of the device will be described below in their preferred technical embodiments. The entire device, with all of its described component parts, is depicted in FIGS. 13*a* to 13*c*.

The intrarectal anchor balloon 1 and the transanal segment 2 are preferably formed from a common tube element. This module is preferably fabricated by blow molding. The material preferably used for this module is polyurethane (PUR) with chemical-physical characteristics and elasticity-mechanical characteristics that are comparable to those of the material "Pellethane 2363" made by Dow Chemical Corporation, particularly with the Shore hardness 80A to 60D. In addition to PUR, soft films can also be produced or processed from PVC and/or LDPE by blow molding.

Conditionally suitable balloon elements that are completely, or nearly completely, preshaped to their subsequent working size can also be produced by dip molding, for example from latex, silicone or varieties of synthetic rubber.

Fabrication may also be contemplated from one or more layers of film consisting of the aforesaid materials, adhesive-bonded and/or welded together to form spherical structures.

The wall thickness of the intrarectal balloon envelope 1 should be in the range of 10 to 40 micrometers. The maximum transverse diameter of the intrarectal segment 1 when freely, pressurelessly unfolded to the preformed size should be approximately 6-9 cm. The axial length of the intrarectal balloon body 1 is preferably 4-6 cm.

If the transanal segment 2 is made from separate parts, then the necessary thin-walled tubular film layers are also preferably fabricated by blow-molding suitably thin-walled cylindrical balloon bodies or tube bodies. A film welding or gluing process of the kind previously described can also be used. The materials used are preferably identical to those used to fabricate the intrarectal anchor balloon 1. If an elastically rebounding tube element or pipe element 30 is integrated, then this can also be made from dip-molded or injection-molded cylindrical elements. PUR with a hardness of 70A to 90A offers the necessary self-straightening elasticity. Elements made from silicone are less well suited.

The funnel element 3 is preferably made of a material that is identical to, or has exactly the same, Shore hardness as the material of balloon tube 8. It is preferably made by injection molding; alternatively, dip molding may also be contemplated.

The material should exhibit reliable elastic re-straightening properties after temporary mechanical deformation, and should also appear as soft and "body-friendly" as possible. It should further lend itself to adhesive bonding with common solvents or glues. The necessary mechanical and chemical properties are furnished, for example, by polyurethanes with Shore hardnesses of 70 to 90. For example, materials with physical-chemical properties like those of the Pellethane 2363 family can be used.

To make it easier to mount on/in the balloon film 8, the funnel element 3 can be provided on its surface with circular preformations (both convex and concave). In the axial direction, in the region of the inner surface or the funnel lumen, longitudinally extending recesses can be fabricated to serve as grooves, and receive any supply lines 32 (balloon filling or irrigation lumens) introduced through the transanal segment 2 from the proximal direction. Special longitudinally extending notches can also be arranged in such a way that the funnel element 3 can be deformed to a slenderer configuration by moderate manual pressure as it is inserted in the anus, and in the rectum will spontaneously straighten out to its original shape by virtue of its mechanical restoring force.

The funnel element 3 preferably is fashioned as olive-shaped, suppository-shaped, cigar-shaped or torpedo-shaped. The maximum outer diameter should be between 4 and 5 cm; the stool-receiving inner lumen should have an inner diameter of no less than 3 cm. The length of the funnel element 3 should be in the range of 3 to 5 cm.

For convenient assembly, the connector element 4 is configured at its distal end with suitable grooves, annular protrusions and diameter offsets to receive the particular transanal elements 2 needed. Suitable preformations for receiving and connecting to the drainage or discharge tube, which preferably discharges to a bag, can be preshaped at the proximal end. The connector element 4 should be made from a deformable material that is as self-straightening as possible, with properties that substantially correspond to those of the funnel element 3.

Connector element 4 can drain both a balloon filling tube and a lumen for intrarectal irrigation to the outside via specific perforations or preformations. A supply line 33 directed toward the bag and provided to irrigate the drainage tube can also be introduced by way of the connector element 4.

The drainage tube 5 comprises a thin-walled, tear-resistant and preferably unexpandable, or only slightly expandable, tube envelope. It is provided with a diameter of approximately 2.5 to 3.5 cm, and in the unfilled state spontaneously collapses into a flat ribbon, or deform to such a ribbon under the application of moderate force, and in this state its contents are adapted to press out manually. Its length should be approximately 20 cm. A wall thickness of approximately 0.1 to 0.2 mm is particularly suitable for this purpose. The length of the discharging or draining tube is about 1.30 m to 1.60 m.

The drainage tube 5 which collapses under slight force to a ribbon-like structure, can also be made from welded film material of the previously cited grades of PUR material. PVC or LDPE, for example, may also be used for this purpose.

In contrast to silicone, which has been the predominant base material heretofore, PUR materials are additionally impermeable to odors. PUR materials also have a very smooth surface, which improves hygiene properties for long dwell times in the patient.

For emptying or cleaning the drainage tube 5, the device can be provided with a barrette-like device 34, which is freely displaceable over the entire length of the drainage tube 5, and which serves to press out stool.

The barrette-like device 34 preferably is similar in shape to a barrette, which surrounds the drainage tube 5 as a preferably closed, ring-like structure. It makes it possible to adjust the drainage lumen to various states of openness. If the tube 5 is shifted to position A inside the barrette 34, the drainage lumen is completely open. If the drainage tube 5 is in position B, its lumen is constricted by the jaws of the barrette 34 such that the tube 5 is pressed together between them into a flat ribbon with no residual lumen. With the barrette in this position, any stool inside the tube 5 can be pushed along manually to a bag 35.

The barrette 34 can also be provided to seal the drainage lumen fluid-tightly, and thus can serve as a temporary seal for when the bag is being changed.

The stool collection bag 35 is designed for a volume capacity of approximately 1 to 2 liters. It is preferably connected to the drainage tube 5 via a connector element 36, which can optionally be provided with a screw thread. The connector element 36 of the tube 5 can comprise a conical plug connector 37, which is inserted into a mating opening in a bag-side connector part 38. The connector part 38, connected to the collection bag 35, can be provided with an external thread. A cap nut 39 can be screwed onto this external thread, and spans a continuously circumferential collar formed onto the connector element 36 and protruding in the radial direction, and thereby presses the conical plug connector 37 firmly into the connector part 38, which can optionally be provided with an inner cone. The tube 5 can thus be connected fluid-tightly to the bag 35. Once the filled bag 35 has been changed, it can preferably be closed leaktightly by means of a closing cap 40 joined to the bag 35 via a flexible link, for example a cable.

If no bag 35 is used, then the plug connector 36, 37 can be sealed during the period of use by means of a gas-permeable but not liquid-permeable seal 41, as shown in FIG. 13c. The seal 41 can consist, for example, of a porous sintered material.

To prevent any backflow of liquid from the bag while the bag is being changed, the bag-side connector part 38 can be provided with a valve mechanism. This can, for example—as illustrated in FIG. 13b—consist of a thin-walled tube element 42 that extends into the bag 35, and whose lumen opens only when material is flowing into the bag, but when there is a slight overpressure in the bag with respect to the environment, sealingly collapses and prevents any outflow from the bag 35. The tube element 42 preferably is provided with a length of approximately 5 to 10 cm.

FIGS. 14a to 14c illustrates a preferred embodiment of the bag 35. This can preferably be provided with an inner bag 43. In this arrangement, the inner bag 43, which is surrounded on all sides by the bag 35, is, for example, equipped with the previously described connector part 38 and analogously receives the drainage tube 5. Outer bag 35, by contrast, can be filled with compressed air, or placed under vacuum via an opening 44.

If the bag 35 is, for example, filled with compressed air by means of a hand pump 45, an irrigation solution introduced into the inner bag beforehand can thus be delivered into the rectum of the patient via the discharge tube 5.

Alternatively to the inner bag concept, the bag 35 can also have a separating wall 51 that divides the bag's interior into two approximately equal-sized compartments 35a and 43a laid out in parallel, in which case a pressure can be built up in the compartment 35a, analogously to the bag 35, that causes the compartment 35a to expand and expels the contents of the compartment 43a, analogously to the contents of inner bag 43, to the patient.

The described compartments 43 and 43a can be filled with prepackaged or specially made-up irrigation solution. Cross section X illustrates the facing compartments 35a, 43a.

Alternatively, a vacuum can be connected to the opening 44 to cause the outer bag 35 to collapse over the inner bag 43, and thus expel its contents into the rectum. The vacuum can be created, for example, by connecting a water jet pump 46 that is connected, in turn, to a water source.

If peristaltic contraction begins in the patient, the latter can adjust the pressure in the outer bag 35 to the environmental pressure. The irrigation solution can then run off into the inner bag 43.

The irrigation solution can then be introduced into the patient again or repeatedly, in the manner of a return flow enema.

Alternatively, the enema can be gravity-driven. In this case, the therapist places a defined volume of irrigation solution in the bag 35 at a suitably high level above the patient. Intake occurs spontaneously. The solution can enter the patient, for example, directly via the discharge tube 5, or can be administered into the rectum via the supply line 32 (see FIG. 6).

Figure 15A:
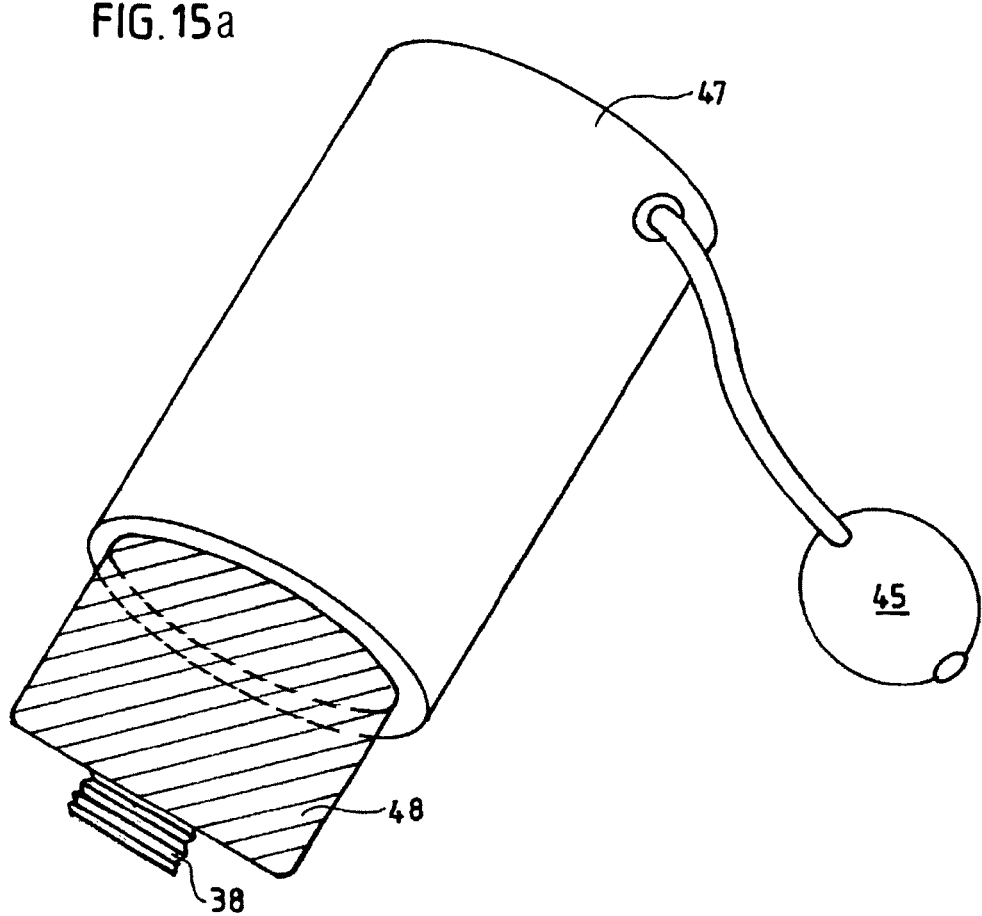
FIG. 15a is a generally perspective view of a device for developing a driving force upon a liquid-containing bag for an enema.
Figure 15B:
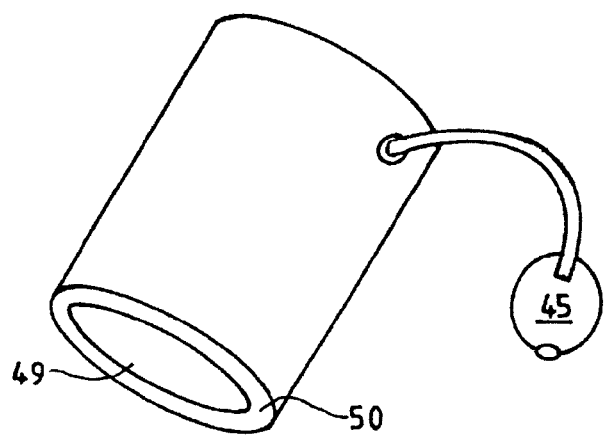
FIG. 15b is a perspective view of a device for developing a driving force for an enema.

As FIGS. 15a and 15b show, to develop a driving force for the enema, it may also be contemplated to employ a cuff-like device 47 of the kind used, for example, for pressure-driven, rapid intravascular infusion (pressure infusion). In this case, a bag-like container 48 holding irrigation solution is inserted into an open central lumen 49 of a cuff 50 to which compressed air can be admitted, and, as the filling pressure in the cuff 50 rises, squeezed out, or emptied into the patient. The required pressure is preferably generated with the hand pump 45. Besides the use of a gaseous medium for building up pressure in the cuff 50, it may also be contemplated to use pressurized liquid media, such as, for example, tapwater or via a connected water column.

The use of the described pressure cuff 50 is especially advantageous in conjunction with pre-made, ready-to-use solutions that are intended to introduce particular therapeutic or palliative substances into the intestine. These can be packaged in bags 48 usable as cuffs.

Self-treating patients are able to void sitting on the toilet, in which case the colorectal irrigation solution can be discharged directly into the toilet via the short drainage tube.

If it is undesirable for the drainage device to remain in the patient during the interval between irrigations, the described enema technique employing a large-lumened discharge tube 5, the described bags 35, 48 and cuffs 50, together with the pressure generators according to the invention, can also be used in combination with the sealing and drainage device described in DE 102004033425 A1 and WO 2007/118621 A1.

In the prior art, the anally sealing balloon 1 and the described balloon arrangements are mounted on a shaft element. As a modification over DE 102004033425 A1 and WO 2007/118621 A1 and within the context of large-volume colorectal irrigation to achieve a continent interval, the shaft element bearing the sealing device can have a correspondingly increased draining inner diameter of approximately 2 to 3 cm. In addition, the length of the balloon-equipped shaft element can advantageously be increased to such an extent that the extracorporeal portion is also suitable for comfortable self-introduction of the irrigation catheter.

The two ends of the everted tube section 8 can, of course, extend approximately coaxially one inside the other and may (each) be connected to a sleeve; in a preferred embodiment of the invention, however, this is not the case.

The invention claimed is:

1. A device for sealing an opening of the colon or rectum of a patient, and for obturating the same and, if required, for removing stool therefrom by a continuous drainage and/or by an intermittent irrigation, into an external, bag-like receptacle, the device comprising:
   at least one inflatable balloon having a generally annular ring-shaped structure, formed from a portion of a flat, everted tube with two ends, the tube portion comprising a radially expanded intrarectal balloon segment for insertion into the rectum, and a transanal segment that is tapered with respect to the radially expanded intrarectal balloon segment, and which remains at least regionally outside the rectum during use,
   wherein said intrarectal balloon segment and said transanal segment have no common compartment,
   wherein said intrarectal and said transanal segments each comprise drainage parts having a central drainage lumen to permit a continuous drainage and/or intermittent irrigation of a stool from the colon or rectum of a patient, and
   wherein one end of the two ends of the tube portion is adapted to be everted and passed through the lumen of said intrarectal balloon segment and advanced as an inner layer within a lumen of an outer layer of the tube portion to an end thereof.

2. The device in accordance with claim 1, wherein only said intrarectal balloon segment is provided with a compartment fillable with a fluid.

3. The device in accordance with claim 1, wherein only said transanal segment is provided with a compartment fillable with a fluid.

4. The device in accordance with claim 1, wherein separation of said segments is effected by durably, sealingly, closing an envelope of said intrarectal balloon segment on, or by means of, a funnel element.

5. The device in accordance with claim 1, wherein a separation of said segments in a region of a proximal end of said intrarectal balloon segment is provided by directly connecting an outer layer of the everted tube portion to a surface portion of said transanal segment.

6. The device in accordance with claim 1 and further comprising an element for obturating a drainage lumen in a region of said transanal segment.

7. The device in accordance with claim 1, wherein during intervals between enemas, the device indwelling in the patient is adapted to perform a rectal-anal sealing function wherein the drainage lumen is obturated at its proximal end, outside the anus, so as to be liquid-tight but permit the passage of gas.

8. The device in accordance with claim 1, wherein in the region of a proximal end of said intrarectal balloon, the balloon is fixed to surfaces of portions of said transanal segment.

9. The device in accordance with claim 1, wherein said transanal segment forms a separately fillable compartment adapted to be filled to improve a seal with respect to an anus by radial expansion of the outer envelope, while under forced filling the drainage lumen is adapted to be additionally constricted toward the center and nearly occluded.

10. The device in accordance with claim 1, wherein a nozzle-like tube or film, is attachable for purposes of drainage into a toilet bowl.

11. The device in accordance with claim 1, wherein a transanal compartment comprising concentric tube elements, and to which a filling medium can be admitted, is separated from said intrarectal balloon segment, whereby the filling of the transanal compartment is independent of the filling of the intrarectal balloon.

12. The device in accordance with claim 11, wherein a volume of the filling medium is equal to about 70-80% of a freely deployed, preformed volume.

13. The device in accordance with claim 1, wherein two ends of said balloon are fixed, parallel to each other, at substantially a same level, to a preanally disposed connector element.

14. The device in accordance with claim 13, wherein said intrarectal balloon segment, in an inside-out, assembled state, exhibits a loge-like preformation for receiving a funnel element.

15. The device in accordance with claim 14, wherein a pipe element unobstructingly connects the funnel element to the connector element and operates to stabilize said transanal segment.

16. The device in accordance with claim 15, wherein said transanal segment comprises a selected one of an elastically self-straightening tube element, and a radially deformable, self-opening basket-woven element, adapted to conform with moderate tension to an anal canal.

17. The device in accordance with claim 16, wherein said transanal segment is double-walled and a chamber formed between said funnel element and said connector element is, via a delivery line from outside the patient, adapted to be selectively evacuated or filled with a filling medium.

18. The device in accordance with claim 17, wherein a drainage lumen extends through said intrarectal funnel element within said intrarectal sealing balloon and debouches directly into a bag-type container via a tube connected to said funnel element and extending through the anal canal.

19. The device in accordance with claim 1, wherein said intrarectal balloon segment and said transanal segment are each provided with a respective compartment fillable with a fluid, the compartments being functionally and spatially separated from each other, and adapted to be separately filled and/or emptied.

20. The device in accordance with claim 19, and further comprising a delivery system for providing the fluid.

21. The device in accordance with claim 19, wherein a selected one of polyurethane and a material having similar technical properties with regard to elasticity and strength, comprises material for said intrarectal balloon segment and/or for a balloon seal.

22. The device in accordance with claim 21, wherein at least one of said intrarectal segment and said transanal segment is of polyurethane.

23. The device in accordance with claim 21, wherein the transanal portion of the device is, at least in part, of a single-ply material.

24. The device in accordance with claim 21, wherein said transanal segment is provided with, in addition to a one- or two-ply tube layer, an additional functional element adapted to counteract axial torsion, or twisting-induced occlusion, of said segment.

25. A device for sealing an opening of the colon or rectum of a patient, and for obturating the same and, if required, for removing stool therefrom by a continuous drainage and/or by an intermittent irrigation, into an external, bag-like receptacle, the device comprising:
- at least one inflatable balloon having a generally annular ring-shaped structure, formed from a portion of a flat, everted tube with two ends, the tube portion comprising a radially expanded intrarectal balloon segment for insertion into the rectum, and a transanal segment that is tapered with respect to the radially expanded intrarectal balloon segment, and which remains at least regionally outside the rectum during use,
- wherein said intrarectal balloon segment and said transanal segment have no common compartment,
- wherein said intrarectal and said transanal segments each comprise drainage parts having a central drainage lumen to permit a continuous drainage and/or intermittent irrigation of a stool from the colon or rectum of a patient, and
- wherein separation of said segments is effected by durably, sealingly, closing an envelope of said intrarectal balloon segment on, or by means of, a funnel element.

26. A device for sealing an opening of the colon or rectum of a patient, and for obturating the same and, if required, for removing stool therefrom by a continuous drainage and/or by an intermittent irrigation, into an external, bag-like receptacle, the device comprising:
- at least one inflatable balloon having a generally annular ring-shaped structure, formed from a portion of a flat, everted tube with two ends, the tube portion comprising a radially expanded intrarectal balloon segment for insertion into the rectum, and a transanal segment that is tapered with respect to the radially expanded intrarectal balloon segment, and which remains at least regionally outside the rectum during use,
- wherein said intrarectal balloon segment and said transanal segment have no common compartment,
- wherein said intrarectal and said transanal segments each comprise drainage parts having a central drainage lumen to permit a continuous drainage and/or intermittent irrigation of a stool from the colon or rectum of a patient, and
- wherein a separation of said segments in a region of a proximal end of said intrarectal balloon segment is provided by directly connecting an outer layer of the everted tube portion to a surface portion of said transanal segment.

* * * * *